US008507196B1

(12) United States Patent
Alizon et al.

(10) Patent No.: US 8,507,196 B1
(45) Date of Patent: *Aug. 13, 2013

(54) NUCLEIC ACID PROBE OF HUMAN IMMUNODEFICIENCY VIRUS TYPE 1 (HIV-1), AND A METHOD AND KIT EMPLOYING THIS PROBE FOR DETECTING THE PRESENCE OF NUCLEIC ACID OF HIV-1

(75) Inventors: Marc Alizon, Paris (FR); Francoise Barre Sinoussi, Clamart (FR); Pierre Sonigo, Paris (FR); Pierre Tiollais, Paris (FR); Jean-Claude Chermann, Cassis (FR); Luc Montagnier, Le Plessis Robinson (FR); Simon Wain-Hobson, Montigny le Bretonneux (FR)

(73) Assignees: Institut Pasteur, Paris (FR); Centre National de la Recherche Scientifique, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/051,226

(22) Filed: Apr. 23, 1993

Related U.S. Application Data

(60) Continuation of application No. 07/158,652, filed on Feb. 22, 1988, now Pat. No. 7,217,508, which is a division of application No. 06/771,248, filed on Aug. 30, 1985, now abandoned, application No. 08/051,226, which is a continuation-in-part of application No. 07/999,410, filed on Dec. 31, 1992, which is a continuation of application No. 07/499,210, filed on Mar. 19, 1990, now abandoned, which is a continuation of application No. 06/771,230, filed on Aug. 30, 1985, now abandoned, which is a continuation-in-part of application No. 06/706,562, filed on Feb. 28, 1985, now abandoned, which is a continuation-in-part of application No. 06/558,109, filed on Dec. 5, 1983, now abandoned.

(30) Foreign Application Priority Data

Sep. 15, 1983 (GB) .................................... 8324800
Sep. 6, 1984 (ZA) .................................... 84/7005
Sep. 19, 1984 (GB) .................................... 8423659

(51) Int. Cl.
*C07H 21/02* (2006.01)
(52) U.S. Cl.
USPC ............................................ 435/6.1; 435/975
(58) Field of Classification Search
USPC ....................... 435/5, 6, 975; 536/23.1, 23.72
See application file for complete search history.

(56) References Cited

U.S. PATENT DOCUMENTS

| 4,520,113 | A |   | 5/1985 | Gallo et al. ...................... 435/5 |
| 4,629,783 | A |   | 12/1986 | Cosand .......................... 530/324 |
| 4,677,054 | A | * | 6/1987 | White et al. ..................... 435/6 |
| 4,708,818 | A |   | 11/1987 | Montagnier et al. ............... 435/5 |
| 4,725,669 | A |   | 2/1988 | Essex et al. ..................... 530/322 |
| 4,808,536 | A |   | 2/1989 | Chang et al. ..................... 435/5 |
| 5,156,949 | A |   | 10/1992 | Luciw et al. |
| 5,665,536 | A |   | 9/1997 | Goldstein et al. ................. 435/5 |
| 6,001,977 | A | * | 12/1999 | Chang et al. .................... 530/389.4 |
| 6,531,276 | B1 |  | 3/2003 | Luciw et al. |
| 6,627,395 | B1 |  | 9/2003 | Montagnier et al. |

FOREIGN PATENT DOCUMENTS

| EP | 0 113 078 | 7/1984 |
| EP | 0 115 459 | 8/1984 |
| EP | 0 199 301 | 10/1986 |
| EP | 0 258 404 B1 | 3/1988 |
| WO | WO 84/04327 | 11/1984 |
| WO | WO 87/05399 | 9/1987 |
| WO | WO 91/04051 | 4/1991 |

OTHER PUBLICATIONS

L. Ratner et al. (1985) Nature 313: 636-637, [Exhibit 2].*
S. Wain-Hobson et al. (1985) Cell 40:9-17. [Exhibit 3].*
L. Ratner et al. (1985) Nature 313: 277-284. [Exhibit 4].*
R. Sanchez-Pescador et al. (1985) Science 227: 484-492, [Exhibit 5].*
M. Guyader et al. (1987) Nature 326: 662-669. [Exhibit 7].*
F. Clavel et al. (1986) Science 233:343-346, [Exhibit 8].*
M.A. Muesing et al. (1985) Nature 313:450-458. [Exhibit 9].*
M. Alizon et al. (1984) Nature 312: 757-760. [Exhibit 10].*
B.H. Hahn et al. (1984) Nature 312: 166-169.*
Richterich, Peter, "Estimation of errors in 'Raw' DNA sequences: a validation study", Genome Research (1998) 8:251-259.*
Hogrefe, http://www.trilinkbiotech.com/tech/pdf/A%20Short%20History%20of%20Oligonucleotide%20Synthesis.pdf, accessed 2004.*
Sch üpbach et al., *Science*, 224, 503-505 (1984).
Kalyanaraman et al., *Science*, 225, 321-323 (1984).
Robey et al., *Science*, 228, 593-595 (1985).
Allan et al., *Science*, 228, 1091-1094 (1985).
Crowl et al., *Chemical Abstracts*, 103, p. 190, No. 154983e (1985).
Montagnier et al., *Chemical Abstracts*, 103, p. 263, No. 34641v (1985).
Weiss et al., *Nature*, 316, 69-72 (1985).
Barin et al., *Science*, 228, 1094-1096 (1985).
Wain-Hobson et al., *Cell*, 40, 9-17 (1985).
Muesing et al., *Nature*, 313, 450-458 (1985).
Schneider et al., *Chemical Abstracts*, 103, p. 430, No. 52370k (1985).
Sarngadharan et al., *Chemical Abstracts*, 103, p. 551, No. 121329t (1985).
Alizon et al., *Nature*, 312, 757-760 (1984).
Chang et al., *Nature*, 315, 151-154 (1985).
Chang et al., *Biotechnology*, 3, 905-909 (1985).
Ratner et al., *Nature*, 313, 277-284 (1985).

(Continued)

*Primary Examiner* — Christopher M. Babic
(74) *Attorney, Agent, or Firm* — Law Office of Salvatore Arrigo and Scott Lee, LLP

(57) ABSTRACT

This invention is in the field of lymphadenopathy virus. This invention relates to a diagnostic means and method to detect the presence of DNA, RNA, or antibodies of the lymphadenopathy retrovirus associated with the acquired immune deficiency syndrome or of the lymphadenopathy syndrome by the use of DNA fragments or the peptides encoded by said DNA fragments. The invention further relates to the DNA fragments, vectors comprising them, and the proteins expressed.

4 Claims, 27 Drawing Sheets

(56) References Cited

OTHER PUBLICATIONS

Dreesman et al., *Nature*, 295, 158-160 (1982).
Kitchen et al., *Nature*, 312, 367-369 (1984).
Essex et al., *Science*, 220, 859-862 (1983).
Seiki et al., *Proc. Natl. Acad. Sci.*, USA, 80, 3618-3622 (1983).
*Biotechnol. Newswatch*, vol. 5, p. 3, abstract No. 03-10-003226 (1985).
Paper No. 300 in Interference No. 102,822; APJs Metz, Pate, and Martin; Mar. 9, 2001; pp. 1-6.
Paper No. 271 in Interference No. 102,822; APJs Metz, Pate, and Martin; Apr. 21, 1999; pp. 1-3.
Paper No. 282 in Interference No. 102,822; APJs Metz, Pate, and Martin; Jul. 30, 1999; pp. 1-2.
Paper No. 289 in Interference No. 102,822; APJs Metz, Pate, and Martin; Oct. 19, 1999; pp. 1-3.
Claims 30, 31, 57-61, 109-115, and 132 in Interference No. 102,822.

\* cited by examiner

```
              N  R  G  E  Q  E  M  E  P  V  D  P  R  L  E  P  W  K  H  P  G  S  Q  P  K
                T  F  E  S  K  K  W  S  Q  *  I  L  D  *  S  P  G  S  I  Q  E  V  S  L
              CAACAGAGGAGAGCAAGAAATGGAGCCAGTAGATCCTAGACTAGAGCCCTGGAAGCATCCAGGAAGTCAGCCTAA
                  5290      5300      5310      5320      5330      5340      5350

P  S  L  F  H  N  K  S  L  R  H  L  L  W  Q  E  E  A  E  T  A  T  K  T  S
            Q  V  C  F  T  T  K  A  L  G  I  S  Y  G  R  K  K  R  R  Q  R  R  R  P  P
              K  F  V  S  Q  Q  K  P  *  A  S  P  M  A  G  R  S  G  D  S  D  E  D  L  L
              CCAAGTTTGTTTCACAACAAAAGCCCTTAGGCATCTCCTATGGCAGGAAGAAGCGGAGACAGCGACGAAGACCTCCT
                  5410      5420      5430      5440      5450      5460      5470

S  T  C  N  A  T  Y  T  N  S  N  S  S  I  S  S  S  N  N  N  S  N  S  C  V
            V  H  V  M  Q  P  I  Q  I  A  I  A  A  L  V  V  A  I  I  I  A  I  V  V  W
              Y  M  *  C  N  L  Y  K  *  Q  *  Q  H  *  *  *  Q  *  *  *  Q  *  L  C  C
              AGTACATGTAATGCAACCTATACAAATAGCAATAGCAGCATTAGTAGTAGCAATAATAATAGCAATAGTTGTGTGG
                  5530      5540      5550      5560      5570      5580      5590

N  R  Q  V  N  *  *  T  N  R  K  S  R  R  Q  W  Q  *  E  *  R  R  N  I  S
            I  D  R  L  I  D  R  L  I  E  R  A  E  D  S  G  N  E  S  E  G  E  I  S  A
              *  T  G  *  L  I  D  *  *  K  E  Q  K  T  V  A  M  R  V  K  E  K  Y  Q  H
              AATAGACAGGTTAATTGATAGACTAATAGAAAGAGCAGAAGACAGTGGCAATGAGAGTGAAGGACAAATATCAGCA
                  5650      5660      5670      5680      5690      5700      5710

Y  *  *  S  V  V  L  Q  K  N  C  G  S  Q  S  I  M  G  Y  L  C  G  R  K  Q
            I  D  D  L  *  C  Y  R  K  I  V  G  H  S  L  L  W  G  T  C  V  E  G  S  N
              L  M  I  C  S  A  T  E  K  L  W  V  T  V  Y  Y  G  V  P  V  W  K  E  A  T
              TATTGATGATCTGTAGTGCTACAGAAAAAATTGTGGGTCACAGTCTATTATGGGGTACCTGTGTGGAAGGAAGCCAAC
                  5770      5780      5790      5800      5810      5820      5830

R  Y  I  M  F  G  P  H  M  P  V  Y  P  Q  T  P  T  H  K  K  *  Y  W  *  M
            G  T  *  C  L  G  H  T  C  L  C  T  H  R  P  Q  P  T  R  S  S  I  G  K  C
              V  H  N  V  W  A  T  H  A  C  V  P  T  D  P  N  P  Q  E  V  V  L  V  [N  V]
              AGGTACATAATGTTTGGGCCACACATGCCTGTGTACCCACAGACCCCAACCCACAAGAAGTAGTATTGGTAAATGT
                  5890      5900      5910      5920      5930      5940      5950

C  M  R  I  *  S  V  Y  G  I  K  A  *  S  H  V  *  N  *  P  H  S  V  L  V
            A  *  G  Y  N  Q  P  M  G  S  K  P  K  A  M  C  K  I  N  P  T  L  C  *  F
              H  E  D  I  I  S  L  W  D  Q  S  L  K  P  C  V  K  L  T  P  L  C  V  S  L
              TGCATGAGGATATAATCAGTTTATGGGATCAAAGCCTAAAGCCATGTCTAAAATTAACCCCACTCTGTGTTAGTTT
                  6010      6020      6030      6040      6050      6060      6070

I  P  I  V  V  A  G  K  *  *  W  R  K  E  R  *  K  T  A  L  S  I  S  A  Q
            Y  Q  *  *  *  R  G  N  D  D  G  E  R  R  D  K  K  L  L  F  Q  Y  Q  H  K
              T  [N  S  S]  S  G  E  M  M  M  E  K  G  E  I  K  [N  C  S]  F  [N  I  S]  T  S
              ATACCAATAGTAGTAGCGGGGAAATGATGATGGAGAAAGGAGAGATAAAAAACTGCTCTTTCAATATCAGCACAAG
                  6130      6140      6150      6160      6170      6180      6190

L  I  *  Y  Q  *  I  M  I  L  P  A  I  R  *  Q  V  V  T  P  Q  S  L  H  R
            *  Y  N  T  N  R  *  *  Y  Y  Q  L  Y  V  D  K  L  *  H  L  S  H  Y  T  G
              D  I  I  P  I  D  [N  D  T]  T  S  Y  T  L  T  S  C  [N  T  S]  V  I  T  Q  A
              TTGATATAATACCAATAGATAATGATACTACCAGCTATACGTTCACAAGTTGTAACACCTCAGTCATTACACAGGG
                  6250      6260      6270      6280      6290      6300      6310

```
          P  G  S  Q  P  K  T  A  C  I  T  C  Y  C  K  K  C  C  F  H  C
       Q  E  V  S  L  K  L  L  V  P  L  A  I  V  K  S  V  A  F  I  A
     CAGGAAGTCAGCCTAAAACTGCTTGTACCACTTGCTATTGTAAAAAGTGTTGCTTTCATTG
          5350      5360      5370      5380      5390      5400

A  T  K  T  S  S  R  Q  S  D  S  S  S  F  S  I  K  A  V  S
          Q  R  R  R  P  P  Q  G  S  Q  T  H  Q  V  S  L  S  K  Q  *  V
           S  D  E  D  L  L  K  A  V  R  L  I  K  F  L  Y  Q  S  S  K  *
     AGCGACGAAGACCTCCTCAAGGCAGTCAGACTCATCAAGTTTCTCTATCAAAGCAGTAAGT
          5470      5480      5490      5500      5510      5520

S  N  S  C  V  V  H  S  N  H  R  I  *  E  N  I  K  T  K  K
          I  A  I  V  V  W  S  I  V  I  I  E  Y  R  K  I  L  R  Q  R  K
           *  Q  *  L  C  G  P  *  *  S  *  N  I  G  K  Y  *  D  K  E  K
     TAGCAATAGTTGTGTGGTCCATAGTAATCATAGAATATAGGAAAATATTAAGACAAAGAAA
          5590      5600      5610      5620      5630      5640

R  R  N  I  S  T  C  G  D  G  G  G  N  G  A  P  C  S  L  G
            G  E  I  S  A  L  V  E  M  G  V  E  M  G  H  H  A  P  W  D
           K  E  K  Y  Q  H  L  W  R  W  G  W  K  W  G  T  M  L  L  G  I
     AAGGAGAAATATCAGCACTTGTGGAGATGGGGGTGGAAATGGGGCACCATGCTCCTTGGA
          5710      5720      5730      5740      5750      5760

C  G  P  K  Q  P  P  L  Y  F  V  H  Q  M  L  K  H  M  I  Q
          V  E  G  S  N  H  H  S  I  L  C  I  R  C  *  S  I  *  Y  R
           V  W  K  E  A  T  T  T  L  F  C  A  S  D  A  K  A  Y  D  T  E
     TGTGGAAGGAAGCAACCACCACTCTATTTTGTGCATCAGATGCTAAAGCATATGATACAG
          5830      5840      5850      5860      5870      5880

*  Y  W  *  M  *  Q  K  I  L  T  C  G  K  M  T  W  *  N  R
            S  I  G  K  C  D  R  K  F  *  H  V  E  K  *  H  G  R  T  D
           V  V  L  V  N  V  T  E  N  F  N  M  W  K  N  D  M  V  E  Q  M
     TAGTATTGGTAAATGTGACAGAAAATTTTAACATGTGGAAAAATGACATGGTAGAACAGA
          5950      5960      5970      5980      5990      6000

H  S  V  L  V  *  S  A  L  I  W  G  M  L  L  I  P  I  V  V
            T  L  C  *  F  K  V  H  *  F  G  E  C  Y  *  Y  Q  *  *  *
           P  L  C  V  S  L  K  C  T  D  L  G  N  A  T  N  T  N  S  S  N
     CACTCTGTGTTAGTTTAAAGTGCACTGATTTGGGGAATGCTACTAATACCAATAGTAGTA
          6070      6080      6090      6100      6110      6120

S  I  S  A  Q  A  *  E  V  R  C  R  K  N  M  H  F  F  I  N
            Q  Y  Q  H  K  H  K  R  *  G  A  E  R  I  C  I  F  L  *  T
           F  N  I  S  T  S  I  R  G  K  V  Q  K  E  Y  A  F  F  Y  K  L
     TCAATATCAGCACAAGCATAAGAGGTAAGGTGCAGAAAGAATATGCATTTTTTTATAAAC
          6190      6200      6210      6220      6230      6240

Q  S  L  H  R  P  V  Q  R  Y  P  L  S  Q  F  P  Y  I  I  V
            S  H  Y  T  G  L  S  K  G  I  L  *  A  N  S  H  T  L  L  C
           S  V  I  T  Q  A  C  P  K  V  S  F  E  P  I  P  I  H  Y  C  A
     CAGTCATTACACAGGCCTGTCCAAAGGTATCCTTTGAGCCAATTCCCATACATTATTGTG
          6310      6320      6330      6340      6350      6360

```
    P  C  W  F  C  D  S  K  M  *  *  *  D  V  Q  W  N  R  T  M  Y  K  C  Q
     P  A  G  F  A  I  L  R  C  N  N  K  T  F  N  G  T  G  P  C  T  N  V  S
CCCCGGCTGGTTTTGCGATTCTAAAATGTAATAATAAGACGTTCAATGGAACAGGACCATGTACAAATGTCAGC
        6370      6380      6390      6400      6410      6420      6430

C  C  *  M  A  V  *  Q  K  K  R  *  L  D  L  P  I  S  Q  T  M  L  K  P
     A  V  E  W  Q  S  S  R  R  R  G  S  N  *  I  C  Q  F  H  R  Q  C  *  N  H
      L  L  N  G  S  L  A  E  E  E  V  V  I  R  S  A  N  F  T  D  N  A  K  T
TGCTGTTGAATGGCAGTCTAGCAGAAGAAGAGGTAGTAATTAGATCTGCCAATTTCACAGACAATGCTAAAACCA
        6490      6500      6510      6520      6530      6540      6550

P  T  T  I  Q  E  K  V  S  V  S  R  G  D  Q  G  E  H  L  L  Q  *  E  K  *
     Q  Q  Q  Y  K  K  K  Y  P  Y  P  E  G  T  R  E  S  I  C  Y  N  R  K  N  R
      N  N  N  T  R  K  S  I  R  I  Q  R  G  P  G  R  A  F  V  T  I  G  K  I
CCAACAACAATACAAGAAAAAGTATCCGTATCCAGAGGGGACCAGGGAGAGCATTGTTACAATAGGAAAAATAG
        6610      6620      6630      6640      6650      6660      6670

M  P  L  *  N  R  *  L  A  N  *  E  N  N  L  E  I  I  K  Q  *  S  L  S  N
     C  H  F  K  T  D  S  *  Q  I  K  R  T  I  W  K  *  *  N  N  N  L  *  A  I
      A  T  L  K  Q  I  A  S  K  L  R  E  Q  F  G  N  N  K  I  I  I  F  K  Q
ATGCCACTTTAAAACAGATAGCTAGCAAATTAAGAGAACAATTTGGAAATAATAAAACAATAATCTTTAAGCAA
        6730      6740      6750      6760      6770      6780      6790

E  G  N  F  S  T  V  I  Q  H  N  C  L  I  V  L  G  L  I  V  L  G  V  L  K
     R  G  I  F  L  L  *  F  N  T  T  V  *  *  Y  L  V  *  *  Y  L  E  Y  *  R
      G  E  F  F  Y  C  N  S  T  Q  L  F  N  S  T  W  F  N  S  T  W  S  T  E
GAGGGGAATTTTTCTACTGTAATTCAACACAACTGTTTAATAGTACTTGGTTTAATAGTACTTGGAGTACTGAAG
        6850      6860      6870      6880      6890      6900      6910

E  *  N  N  L  *  T  C  G  R  K  *  E  K  Q  C  M  P  L  P  S  A  D  K  L
     N  K  T  I  Y  K  H  V  A  G  S  R  K  S  N  V  C  P  S  H  Q  R  T  N  *
      I  K  Q  F  I  N  M  W  Q  E  V  G  K  A  M  Y  A  P  P  I  S  G  Q  I
GAATAAAACAATTTATAAACATGTGGCAGGAAGTAGGAAAAGCAATGTATGCCCCTCCCATCAGCGGACAAATTA
        6970      6980      6990      7000      7010      7020      7030

V  I  T  T  M  G  P  R  S  S  D  L  E  E  E  I  *  G  T  I  G  E  V  N  Y
     *  *  Q  Q  W  V  R  D  L  Q  T  W  R  R  R  Y  E  G  Q  L  E  K  *  I  I
      N  N  N  N  G  S  E  I  F  R  P  G  G  G  D  M  R  D  N  W  R  S  E  L
GTAATAACAACAATGGGTCCGAGATCTTCAGACCTGGAGGAGGAGATATGAGGGACAATTGGAGAAGTGAATTAT
        7090      7100      7110      7120      7130      7140      7150

P  R  Q  R  E  E  W  C  R  E  K  K  E  Q  W  E  *  E  L  C  S  L  G  S  W
     Q  G  K  E  K  S  G  A  E  R  K  K  S  S  G  N  R  S  F  V  P  W  V  L  G
      K  A  K  R  R  V  V  Q  R  E  K  R  A  V  G  I  G  A  L  F  L  G  F  L
CCAAGGCAAAGAGAAGAGTGGTGCAGAGAGAAAAAAGAGCAGTGGGAATAGGAGCTTTGTTCCTTGGGTTCTTGG
        7210      7220      7230      7240      7250      7260      7270

Y  R  P  D  N  Y  C  L  V  *  C  S  S  R  T  I  C  *  G  L  L  R  R  N  S
     T  G  Q  T  I  I  V  W  Y  S  A  A  A  E  Q  F  A  E  G  Y  *  G  A  T  A
      Q  A  R  Q  L  L  S  G  I  V  Q  Q  Q  N  N  L  L  R  A  I  E  A  Q  Q
TACAGGCCAGACAATTATTGTCTGGTATAGTGCAGCAGCAGAACAATTTGCTGAGGGCTATTGAGGCGCAACAGC
        7330      7340      7350      7360      7370      7380      7390

```
              N  R  T  M  Y  K  C  Q  H  S  T  M  Y  T  W  N  *  N  S  S  I  N  S  T
              T  G  P  C  T  N  V  S  T  V  Q  C  T  H  G  I  R  P  V  V  S  T  Q  L
              AACAGGACCATGTACAAATGTCAGCACAGTACAATGTACACATGGAATTAGGCCAGTAGTATCAACTCAAC
                  6420      6430      6440      6450      6460      6470      6480

P  I  S  Q  T  M  L  K  P  *  *  Y  S  *  T  N  L  *  K  L  I  V  Q  D
              Q  F  H  R  Q  C  *  N  H  N  S  T  A  E  P  I  C  R  N  *  L  Y  K  T
              N  F  T  D  N  A  K  T  I  I  V  Q  L  N  Q  S  V  E  I  N  C  T  R  P
              CAATTTCACAGACAATGCTAAAACCATAATAGTACAGCTGAACCAATCTGTAGAAATTAATTGTACAAGAC
                  6540      6550      6560      6570      6580      6590      6600

F  H  L  L  Q  *  E  K  *  E  I  *  D  K  H  I  V  T  L  V  E  Q  N  G
              S  I  C  Y  N  R  K  N  R  K  Y  E  T  S  T  K  *  H  *  *  S  K  M  E
              A  F  V  T  I  G  K  I  G  N  M  R  Q  A  H  C  N  I  S  R  A  K  W  N
              AGCATTTGTTACAATAGGAAAAATAGGAAATATGAGACAAGCACATTGTAACATTAGTAGAGCAAAATGGA
                  6660      6670      6680      6690      6700      6710      6720

I  I  K  Q  *  S  L  S  N  P  Q  E  G  T  Q  K  L  *  R  T  V  L  I  V
              *  *  N  N  L  *  A  I  L  R  R  G  P  R  N  C  N  A  Q  F  *  L  W
              N  K  I  I  I  F  K  Q  S  S  G  G  D  P  E  I  V  T  H  S  F  N  C  G
              TAATAAAACAATAATCTTTAAGCAATCCTCAGGAGGGGACCCAGAAATTGTAACGCACAGTTTTAATTGTG
                  6780      6790      6800      6810      6820      6830      6840

C  L  I  V  L  G  V  L  K  G  Q  I  T  L  K  E  V  T  Q  S  H  S  H  A
              V  *  *  Y  L  E  Y  *  R  V  K  *  H  *  R  K  *  H  N  H  T  P  M  Q
              P  N  S  T  W  S  T  E  G  S  N  N  T  E  G  S  D  I  T  L  P  C  R
              TTTTAATAGTACTTGGAGTACTGAAGGGTCAAATAACACTGAAGGAAGTGACACAATCACACTCCCATGCA
                  6900      6910      6920      6930      6940      6950      6960

M  P  L  P  S  A  D  K  L  D  V  H  Q  I  L  Q  G  C  Y  *  Q  E  M  V
              C  P  S  H  Q  R  T  N  *  M  F  I  K  Y  Y  R  A  A  I  N  K  R  W  W
              A  P  P  I  S  G  Q  I  R  C  S  S  N  I  T  G  L  L  L  T  R  D  G  G
              TGCCCCTCCCATCAGCGGACAAATTAGATGTTCATCAAATATTACAGGGCTGCTATTAACAAGAGATGGTG
                  7020      7030      7040      7050      7060      7070      7080

*  G  T  I  G  E  V  N  Y  I  N  I  K  *  *  K  L  N  H  *  E  *  H  P
              E  G  Q  L  E  K  *  I  I  *  I  *  S  S  K  N  *  T  I  R  S  S  T  H
              R  D  N  W  R  S  E  L  Y  K  Y  K  V  V  K  I  E  P  L  G  V  A  P  T
              GAGGGACAATTGGAGAAGTGAATTATATAAATATAAAGTAGTAAAAATTGAACCATTAGGAGTAGCACCCA
                  7140      7150      7160      7170      7180      7190      7200

*  E  L  C  S  L  G  S  W  E  Q  Q  E  A  L  W  A  H  G  Q  *  R  *  R
              R  S  F  V  P  W  V  L  G  S  S  R  K  H  Y  G  R  T  V  N  D  A  D  G
              G  A  L  F  L  G  F  L  G  A  A  G  S  T  M  G  A  R  S  M  T  L  T  V
              AGGAGCTTTGTTCCTTGGGTTCTTGGGAGCAGCAGGAAGCACTATGGGCGCACGGTCAATGACGCTGACGG
                  7260      7270      7280      7290      7300      7310      7320

C  *  G  L  L  R  R  N  S  I  C  C  N  S  Q  S  G  A  S  S  S  S  R  Q
              A  E  G  Y  *  G  A  T  A  S  V  A  T  H  S  L  G  H  Q  A  A  P  G  K
              L  R  A  I  E  A  Q  Q  H  L  L  Q  L  T  V  W  G  I  K  Q  L  Q  A  R
              GCTGAGGGCTATTGAGGCGCAACAGCATCTGTTGCAACTCACAGTCTGGGGCATCAAGCAGCTCCAGGCAA
                  7380      7390      7400      7410      7420      7430      7440

```
          N P G C G K I P K G S T A P G D L G L L W K T H
           I L A V E R Y L K D Q Q L L G I W G C S G K L I
GAATCCTGGCTGTGGAAAGATACCTAAAGGATCAACAGCTCCTGGGGATTTGGGGTTGCTCTGGAAAACTCATT
       7450      7460      7470      7480      7490      7500      7510

W N R F G I T * P G W S G T E K L T I T Q A * Y I
       G T D L E * H D L D G V G Q R N * Q L H K L N T
        E Q I W N N M T W M E W D R E I N N Y T S L I H
TGGAACAGATTTGGAATAACATGACCTGGATGGAGTGGGACAGAGAAATTAACAATTACACAAGCTTAATACAT
       7570      7580      7590      7600      7610      7620      7630

N Y W N * I N G Q V C S I G L T * Q I G C G I * K
       I I G I R * M G K F V E L V * H N K L A V V Y K
        L L E L D K W A S L W N W P N I T N W L W Y I K
AATTATTGGAATTAGATAAATGGGCAAGTTTGTGGAATTGGTTTAACATAACAAATTGGCTGTGGTATATAAAA
       7690      7700      7710      7720      7730      7740      7750

L L Y F L * * I E L G R D I H H Y R F R P T S Q P
       C C T F Y S E * S * A G I F T I I V S D P P P N
        A V L S I V N R V R Q G Y S P L S F Q T H L P T
TTGCTGTACTTTCTATAGTGAATAGAGTTAGGCAGGGATATTCACCATTATCGTTTCAGACCCACCTCCCAACC
       7810      7820      7830      7840      7850      7860      7870

R E T E T D P F D * * T D P * H L S G T I C G A L
       E R Q R Q I H S I S E R I L S T Y L G R S A E P
        R D R D R S I R L V N G S L A L I W D D L R S L
AGAGAGACAGAGACAGATCCATTCGATTAGTGAACGGATCCTTAGCACTTATCTGGGACGATCTGCGGAGCCTT
       7930      7940      7950      7960      7970      7980      7990

T R I V E L L G R R G W E A L K Y W W N L L Q Y W
       R G L W N F W D A G G G K P S N I G G I S Y S I
        E D C G T S G T Q G V G S P Q I L V E S P T V L
ACGAGGATTGTGGAACTTCTGGGACGCAGGGGGTGGGAAGCCCTCAAATATTGGTGGAATCTCCTACAGTATTC
       8050      8060      8070      8080      8090      8100      8110

A I A V A E G T D R V I E V V Q G A C R A I R H I
       P * Q * L R G Q I G L * K * Y K E L V E L F A T
        H S S S * G D R * G Y R S S T R S L * S Y S P H
GCCATAGCAGTAGCTGAGGGGACAGATAGGGTTATAGAAGTAGTACAAGGAGCTTGTAGAGCTATTCGCCACAT
       8170      8180      8190      8200      8210      8220      8230

G W Q V V K K * C G W M A Y C K G K N E T S * A S
       G G K W S K S S V V G W P T V R E R M R R A E P
        V A S G Q K V V W L D G L L * G K E * D E L S Q
GGGTGGCAAGTGGTCAAAAAGTAGTGTGGTTGGATGGCCTACTGTAAGGGAAAGAATGAGACGAGCTGAGCCAG
       8290      8300      8310      8320      8330      8340      8350

S N H K * Q Y S S Y Q C C L C L A R S T R G G G G
       A I T S S N T A A T N A A C A W L F A Q E E E E
        Q S Q V A I Q Q L P M L L V P G * K H K R R R R
AGCAATCACAAGTAGCAATACAGCAGCTACCAATGCTGCTTGTGCCTGGCTAGAAGCACAAGAGGAGGAGGAGG
       8410      8420      8430      8440      8450      8460      8470

```
        W  K  T  H  L  H  H  C  C  A  L  E  C  *  L  E  *  *  I  S
         G  K  L  I  C  T  T  A  V  P  W  N  A  S  W  S  N  K  S  L
CTGGAAAACTCATTTGCACCACTGCTGTGCCTTGGAATGCTAGTTGGAGTAATAAATCTC
    7510      7520      7530      7540      7550      7560

Q  A  *  Y  I  P  *  L  K  N  R  K  T  S  K  K  R  M  N  K
         K  L  N  T  F  L  N  *  R  I  A  K  P  A  R  K  E  *  T  R
          S  L  I  H  S  L  I  E  E  S  Q  N  Q  Q  E  K  N  E  Q  E
CAAGCTTAATACATTCCTTAATTGAAGAATCGCAAAACCAGCAAGAAAAGAATGAACAAG
    7630      7640      7650      7660      7670      7680

C  G  I  *  K  Y  S  *  *  *  *  E  A  W  *  V  *  E  *  F
         V  V  Y  K  N  I  H  N  D  S  R  R  L  G  R  F  K  N  S  F
          W  Y  I  K  I  F  I  M  I  V  G  G  L  V  G  L  R  I  V  F
TGTGGTATATAAAAATATTCATAATGATAGTAGGAGGCTTGGTAGGTTTAAGAATAGTTT
    7750      7760      7770      7780      7790      7800

P  T  S  Q  P  R  G  D  P  T  G  P  K  E  *  K  K  K  V  E
         P  P  P  N  P  E  G  T  R  Q  A  R  R  N  R  R  R  R  W  R
          H  L  P  T  P  R  G  P  D  R  P  E  G  I  E  E  E  G  G  E
CCACCTCCCAACCCCGAGGGGACCCGACAGGCCCGAAGGAATAGAAGAAGAAGGTGGAG
    7870      7880      7890      7900      7910      7920

I  C  G  A  L  C  L  F  S  Y  H  R  L  R  D  L  L  L  I  V
         S  A  E  P  C  A  S  S  A  T  T  A  *  E  T  Y  S  *  L  *
          L  R  S  L  V  P  L  Q  L  P  P  L  E  R  L  T  L  D  C  N
TCTGCGGAGCCTTGTGCCTCTTCAGCTACCACCGCTTGAGAGACTTACTCTTGATTGTA
    7990      8000      8010      8020      8030      8040

L  L  Q  Y  W  S  Q  E  L  K  N  S  A  V  S  L  L  N  A  T
         S  Y  S  I  G  V  R  N  *  R  I  V  L  L  A  C  S  M  P  Q
          P  T  V  L  E  S  G  T  K  E  *  C  C  *  L  A  Q  C  H  S
TCCTACAGTATTGGAGTCAGGAACTAAAGAATAGTGCTGTTAGCTTGCTCAATGCCACA
    8110      8120      8130      8140      8150      8160

A  I  R  H  I  P  R  R  I  R  Q  G  L  E  R  I  L  L  *  D
         L  P  A  T  Y  L  E  E  *  D  R  A  W  K  G  F  C  Y  K  M
          Y  S  P  H  T  *  K  N  K  T  G  L  G  K  D  F  A  I  R  W
CTATTCGCCACATACCTAGAAGAATAAGACAGGGCTTGGAAAGGATTTTGCTATAAGAT
    8230      8240      8250      8260      8270      8280

T  S  *  A  S  S  R  W  G  G  S  S  I  S  R  P  G  K  T  W
         R  A  E  P  A  A  D  G  V  G  A  A  S  R  D  L  E  K  H  G
          E  L  S  Q  Q  Q  M  G  W  E  Q  H  L  E  T  W  K  N  M  E
CGAGCTGAGCCAGCAGCAGATGGGGTGGGAGCAGCATCTCGAGACCTGGAAAAACATGG
    8350      8360      8370      8380      8390      8400

Q  G  G  G  G  G  F  S  S  H  T  S  G  T  F  K  T  N  D  L
         E  E  E  E  V  G  F  P  V  T  P  Q  V  P  L  R  P  M  T  Y
          R  R  R  R  R  W  V  F  Q  S  H  L  R  Y  L  *  D  Q  *  L  T
GAGGAGGAGGAGGTGGGTTTCCAGTCACACCTCAGGTACCTTTAAGACCAATGACTTA
    8470      8480      8490      8500      8510      8520

```
        10         20         30         40         50         60
AAGCTTGCCT TGAGTGCTTC AAGTAGTGTG TGCCCGTCTG TTGTGTGACT CTGGTAACTA
        70         80         90        100        110        120
GAGATCCCTC AGACCCTTTT AGTCAGTGTG GAAAATCTCT AGCAGTGGCG CCCGAACAGG
       130        140        150        160        170        180
GACTTGAAAG CGAAAGGGAA ACCAGAGGAG CTCTCTCGAC GCAGGACTCG GCTTGCTGAA
       190        200        210        220        230        240
GCGCGCACGG CAAGAGGCGA GGGGAGGCGA CTGGTGAGTA CGCCAAAAAT TTTGACTAGC
       250        260        270        280        290        300
GGAGGCTAGA AGGAGAGAGA TGGGTGCGAG AGCGTCAGTA TTAAGCGGGG GAGAATTAGA
       310        320        330        340        350        360
TCGATCGGAA AAAATTCGGT TAAGGCCAGG GGCAAAGAAA AAATATAAAT TAAAACATAT
       370        380        390        400        410        420
AGTATGGGCA AGCAGGGAGC TAGAACGATT CGCTGTTAAT CCTGGCCTGT TAGAAACATC
       430        440        450        460        470        480
AGAAGGCTGT AGACAAATAC TGGGACAGCT ACAACCATCC CTTCAGACAG GATCAGAAGA
       490        500        510        520        530        540
ACTTAGATCA TTATATAATA CAGTAGCAAC CCTCTATTGT GTGCATCAAA GGATAGAGAT
       550        560        570        580        590        600
AAAAGACACC AAGGAAGCTT TAGACAAGAT AGAGGAAGAG CAAAACAAAA GTAAGAAAAA
       610        620        630        640        650        660
AGCACAGCAA GCAGCAGCTG ACACAGGACA CAGCAGCCAG GTCAGCCAAA ATTACCCTAT
       670        680        690        700        710        720
AGTGCAGAAC ATCCAGGGGC AAATGGTACA TCAGGCCATA TCACCTAGAA CTTTAAATGC
       730        740        750        760        770        780
ATGGGTAAAA GTAGTAGAAG AGAAGGCTTT CAGCCCAGAA GTGATACCCA TGTTTTCAGC
       790        800        810        820        830        840
ATTATCAGAA GGAGCCACCC CACAAGATTT AAACACCATG CTAAACACAG TGGGGGGACA
       850        860        870        880        890        900
TCAAGCAGCC ATGCAAATGT TAAAAGAGAC CATCAATGAG GAAGCTGCAG AATGGGATAG
       910        920        930        940        950        960
AGTGCATCCA GTGCATGCAG GGCCTATTGC ACCAGGCCAG ATGAGAGAAC CAAGGGGAAG
       970        980        990       1000       1010       1020
TGACATAGCA GGAACTACTA GTACCCTTCA GGAACAAATA GGATGGATGA CAAATAATCC
      1030       1040       1050       1060       1070       1080
ACCTATCCCA GTAGGAGAAA TTTATAAAAG ATGGATAATC CTGGGATTAA ATAAAATAGT
      1090       1100       1110       1120       1130       1140
```

*FIG. 19*

```
AAGAATGTAT AGCCCTACCA GCATTCTGGA CATAAGACAA GGACCAAAAG AACCCTTTAG
   1150       1160       1170       1180       1190       1200
AGACTATGTA GACCGGTTCT ATAAAACTCT AAGAGCCGAG CAAGCTTCAC AGGAGGTAAA
   1210       1220       1230       1240       1250       1260
AAATTGGATG ACAGAAACCT TGTTGGTCCA AAATGCGAAC CCAGATTGTA AGACTATTTT
   1270       1280       1290       1300       1310       1320
AAAAGCATTG GGACCAGCAG CTACACTAGA AGAAATGATG ACAGCATGTC AGGGAGTGGG
   1330       1340       1350       1360       1370       1380
AGGACCCGGC CATAAGGCAA GAGTTTTGGC TGAAGCAATG AGCCAAGTAA CAAATTCAGC
   1390       1400       1410       1420       1430       1440
TACCATAATG ATGCAAAGAG GCAATTTTAG GAACCAAAGA AAGATTGTTA AGTGTTTCAA
   1450       1460       1470       1480       1490       1500
TTGTGGCAAA GAAGGGCACA TAGCCAGAAA TTGCAGGGCC CCTAGGAAAA AGGGCTGTTG
   1510       1520       1530       1540       1550       1560
GAAATGTGGA AAGGAAGGAC ACCAAATGAA AGATTGTACT GAGAGACAGG CTAATTTTTT
   1570       1580       1590       1600       1610       1620
AGGGAAGATC TGGCCTTCCT ACAAGGGAAG GCCAGGGAAT TTTCTTCAGA GCAGACCAGA
   1630       1640       1650       1660       1670       1680
GCCAACAGCC CCACCAGAAG AGAGCTTCAG GTCTGGGGTA GAGACAACAA CTCCCTCTCA
   1690       1700       1710       1720       1730       1740
GAAGCAGGAG CCGATAGACA AGGAACTGTA TCCTTTAACT TCCCTCAGAT CACTCTTTGG
   1750       1760       1770       1780       1790       1800
CAACGACCCC TCGTCACAAT AAAGATAGGG GGCAACTAA AGGAAGCTCT ATTAGATACA
   1810       1820       1830       1840       1850       1860
GGAGCAGATG ATACAGTATT AGAAGAAATG AGTTTGCCAG GAAGATGGAA ACCAAAAATG
   1870       1880       1890       1900       1910       1920
ATAGGGGGAA TTGGAGGTTT TATCAAAGTA AGACAGTATG ATCAGATACT CATAGAAATC
   1930       1940       1950       1960       1970       1980
TGTGGACATA AAGCTATAGG TACAGTATTA GTAGGACCTA CACCTGTCAA CATAATTGGA
   1990       2000       2010       2020       2030       2040
AGAAATCTGT TGACTCAGAT TGGTTGCACT TTAAATTTTC CCATTAGTCC TATTGAAACT
   2050       2060       2070       2080       2090       2100
GTACCAGTAA AATTAAAGCC AGGAATGGAT GGCCCAAAAG TTAAACAATG GCCATTGACA
   2110       2120       2130       2140       2150       2160
GAAGAAAAAA TAAAAGCATT AGTAGAAATT TGTACAGAAA TGGAAAAGGA AGGGAAAATT
   2170       2180       2190       2200       2210       2220
TCAAAAATTG GGCCTGAAAA TCCATACAAT ACTCCAGTAT TTGCCATAAA GAAAAAAGAC
   2230       2240       2250       2260       2270       2280
AGTACTAAAT GGAGAAAATT AGTAGATTTC AGAGAACTTA ATAAGAGAAC TCAAGACTTC
   2290       2300       2310       2320       2330       2340
TGGGAAGTTC AATTAGGAAT ACCACATCCC GCAGGGTTAA AAAGAAAAAA ATCAGTAACA
   2350       2360       2370       2380       2390       2400
```

FIG. 20

```
GTACTGGATG TGGGTGATGC ATATTTTTCA GTTCCCTTAG ATGAAGACTT CAGGAAGTAT
   2410       2420       2430       2440       2450       2460
ACTGCATTTA CCATACCTAG TATAAACAAT GAGACACCAG GGATTAGATA TCAGTACAAT
   2470       2480       2490       2500       2510       2520
GTGCTTCCAC AGGGATGGAA AGGATCACCA GCAATATTCC AAAGTAGCAT GACAAAAATC
   2530       2540       2550       2560       2570       2580
TTAGAGCCTT TTAGAAAACA AAATCCAGAC ATAGTTATCT ATCAATACAT GGATGATTTG
   2590       2600       2610       2620       2630       2640
TATGTAGGAT CTGACTTAGA AATAGGGCAG CATAGAACAA AAATAGAGGA GCTGAGACAA
   2650       2660       2670       2680       2690       2700
CATCTGTTGA GGTGGGACT TACCACACCA GACAAAAAAC ATCAGAAAGA ACCTCCATTC
   2710       2720       2730       2740       2750       2760
CTTTGGATGG GTTATGAACT CCATCCTGAT AAATGGACAG TACAGCCTAT AGTGCTGCCA
   2770       2780       2790       2800       2810       2820
GAAAAAGACA GCTGGACTGT CAATGACATA CAGAAGTTAG TGGGAAAATT GAATTGGGCA
   2830       2840       2850       2860       2870       2880
AGTCAGATTT ACCCAGGGAT TAAAGTAAGG CAATTATGTA AACTCCTTAG AGGAACCAAA
   2890       2900       2910       2920       2930       2940
GCACTAACAG AAGTAATACC ACTAACAGAA GAAGCAGAGC TAGAACTGGC AGAAAACAGA
   2950       2960       2970       2980       2990       3000
GAGATTCTAA AAGAACCAGT ACATGGAGTG TATTATGACC CATCAAAAGA CTTAATAGCA
   3010       3020       3030       3040       3050       3060
GAAATACAGA AGCAGGGGCA AGGCCAATGG ACATATCAAA TTTATCAAGA GCCATTTAAA
   3070       3080       3090       3100       3110       3120
AATCTGAAAA CAGGAAAATA TGCAAGAACG AGGGGTGCCC ACACTAATGA TGTAAAACAA
   3130       3140       3150       3160       3170       3180
TTAACAGAGG CAGTGCAAAA AATAACCACA GAAAGCATAG TAATATGGGG AAAGACTCCT
   3190       3200       3210       3220       3230       3240
AAATTTAAAC TACCCATACA AAAGGAAACA TGGGAAACAT GGTGGACAGA GTATTGGCAA
   3250       3260       3270       3280       3290       3300
GCCACCTGGA TTCCTGAGTG GGAGTTTGTC AATACCCCTC CTTTAGTGAA ATTATGGTAC
   3310       3320       3330       3340       3350       3360
CAGTTAGAGA AAGAACCCAT AGTAGGAGCA GAAACGTTCT ATGTAGATGG GGCAGCTAGC
   3370       3380       3390       3400       3410       3420
AGGGAGACTA AATTAGGAAA AGCAGGATAT GTTACTAATA GAGGAAGACA AAAAGTTGTC
   3430       3440       3450       3460       3470       3480
ACCCTAACTG ACACAACAAA TCAGAAGACT GAGTTACAAG CAATTCATCT AGCTTTGCAG
   3490       3500       3510       3520       3530       3540
GATTCGGGAT TAGAAGTAAA TATAGTAACA GACTCACAAT ATGCATTAGG AATCATTCAA
   3550       3560       3570       3580       3590       3600
GCACAACCAG ATAAAAGTGA ATCAGAGTTA GTCAATCAAA TAATAGAGCA GTTAATAAAA
   3610       3620       3630       3640       3650       3660
```

FIG. 21

```
AAGCAAAAGG TCTATCTGGC ATGGGTACCA GCACACAAAG GAATTGGAGG AAATGAACAA
    3670       3680       3690       3700       3710       3720
GTAGATAAAT TAGTCAGTGC TGGAATCAGG AAAGTACTAT TTTTAGATGG AATAGATAAG
    3730       3740       3750       3760       3770       3780
GCCCAAGATG AACATGAGAA ATATCACAGT AATTGGAGAG CAATGGCTAG TGATTTTAAC
    3790       3800       3810       3820       3830       3840
CTGCCACCTG TAGTAGCAAA AGAAATAGTA GCCAGCTGTG ATAAATGTCA GCTAAAAGGA
    3850       3860       3870       3880       3890       3900
GAAGCCATGC ATGGACAAGT AGACTGTAGT CCAGGAATAT GGCAACTAGA TTGTACACAT
    3910       3920       3930       3940       3950       3960
TTAGAAGGAA AAGTTATCCT GGTAGCAGTT CATGTAGCCA GTGGATATAT AGAAGCAGAA
    3970       3980       3990       4000       4010       4020
GTTATTCCAG CAGAAACAGG GCAGGAAACA GCATACTTTC TTTTAAAATT AGCAGGAAGA
    4030       4040       4050       4060       4070       4080
TGGCCAGTAA AAACAATACA TACAGACAAT GGCAGCAATT TCACCAGTAC TACGGTTAAG
    4090       4100       4110       4120       4130       4140
GCCGCCTGTT GGTGGGCGGG AATCAAGCAG GAATTTGGAA TTCCCTACAA TCCCCAAAGT
    4150       4160       4170       4180       4190       4200
CAAGGAGTAG TAGAATCTAT GAATAAAGAA TTAAAGAAAA TTATAGGCCA GGTAAGAGAT
    4210       4220       4230       4240       4250       4260
CAGGCTGAAC ATCTTAAGAC AGCAGTACAA ATGGCAGTAT TCATCCACAA TTTTAAAAGA
    4270       4280       4290       4300       4310       4320
AAAGGGGGGA TTGGGGGGTA CAGTGCAGGG GAAAGAATAG TAGACATAAT AGCAACAGAC
    4330       4340       4350       4360       4370       4380
ATACAAACTA AAGAATTACA AAAACAAATT ACAAAAATTC AAAATTTTCG GGTTTATTAC
    4390       4400       4410       4420       4430       4440
AGGGACAGCA GAGATCCACT TTGGAAAGGA CCAGCAAAGC TCCTCTGGAA AGGTGAAGGG
    4450       4460       4470       4480       4490       4500
GCAGTAGTAA TACAAGATAA TAGTGACATA AAAGTAGTGC CAAGAAGAAA AGCAAAGATC
    4510       4520       4530       4540       4550       4560
ATTAGGGATT ATGGAAAACA GATGGCAGGT GATGATTGTG TGGCAAGTAG ACAGGATGAG
    4570       4580       4590       4600       4610       4620
GATTAGAACA TGGAAAAGTT TAGTAAAACA CCATATGTAT GTTTCAGGGA AAGCTAGGGG
    4630       4640       4650       4660       4670       4680
ATGGTTTTAT AGACATCACT ATGAAAGCCC TCATCCAAGA ATAAGTTCAG AAGTACACAT
    4690       4700       4710       4720       4730       4740
CCCACTAGGG GATGCTAGAT TGGTAATAAC AACATATTGG GGTCTGCATA CAGGAGAAAG
    4750       4760       4770       4780       4790       4800
AGACTGGCAT CTGGGTCAGG GAGTCTCCAT AGAATGGAGG AAAAAGAGAT ATAGCACACA
    4810       4820       4830       4840       4850       4860
AGTAGACCCT GAACTAGCAG ACCAACTAAT TCATCTGTAT TACTTTGACT GTTTTTCAGA
    4870       4880       4890       4900       4910       4920
```

FIG. 22

```
CTCTGCTATA AGAAAGGCCT TATTAGGACA TATAGTTAGC CCTAGGTGTG AATATCAAGC
    4930       4940       4950       4960       2970       2980
AGGACATAAC AAGGTAGGAT CTCTACAATA CTTGGCACTA GCAGCATTAA TAACACCAAA
    4990       5000       5010       5020       5030       5040
AAAGATAAAG CCACCTTTGC CTAGTGTTAC GAAACTGACA GAGGATAGAT GGAACAAGCC
    5050       5060       5070       5080       5090       5100
CCAGAAGACC AAGGGCCACA GAGGGAGCCA CACAATGAAT GGACACTAGA GCTTTTAGAG
    5110       5120       5130       5140       5150       5160
GAGCTTAAGA ATGAAGCTGT TAGACATTTT CCTAGGATTT GGCTCCATGG CTTAGGGCAA
    5170       5180       5190       5200       5210       5220
CATATCTATG AAACTTATGG GGATACTTGG GCAGGAGTGG AAGCCATAAT AAGAATTCTG
    5230       5240       5250       5260       5270       5280
CAACAACTGC TGTTTATCCA TTTCAGAATT GGGTGTCGAC ATAGCAGAAT AGGCGTTACT
    5290       5300       5310       5320       5330       5340
CAACAGAGGA GAGCAAGAAA TGGAGCCAGT AGATCCTAGA CTAGAGCCCT GGAAGCATCC
    5350       5360       5370       5380       5390       5400
AGGAAGTCAG CCTAAAACTG CTTGTACCAC TTGCTATTGT AAAAAGTGTT GCTTTCATTG
    5410       5420       5430       5440       5450       5460
CCAAGTTTGT TTCACAACAA AAGCCTTAGG CATCTCCTAT GGCAGGAAGA AGCGGAGACA
    5470       5480       5490       5500       5510       5520
GCGACGAAGA CCTCCTCAAG GCAGTCAGAC TCATCAAGTT TCTCTATCAA AGCAGTAAGT
    5530       5540       5550       5560       5570       5580
AGTACATGTA ATGCAACCTA TACAAATAGC AATAGCAGCA TTAGTAGTAG CAATAATAAT
    5590       5600       5610       5620       5630       5640
AGCAATAGTT GTGTGGTCCA TAGTAATCAT AGAATATAGG AAAATATTAA GACAAAGAAA
    5650       5660       5670       5680       5690       5700
AATAGACAGG TTAATTGATA GACTAATAGA AAGAGCAGAA GACAGTGGCA ATGAGAGTGA
    5710       5720       5730       5740       5750       5760
AGGAGAAATA TCAGCACTTG TGGAGATGGG GGTGGAAATG GGGCACCATG CTCCTTGGGA
    5770       5780       5790       5800       5810       5820
TATTGATGAT CTGTAGTGCT ACAGAAAAAT TGTGGGTCAC AGTCTATTAT GGGGTACCTG
    5830       5840       5850       5860       5870       5880
TGTGGAAGGA AGCAACCACC ACTCTATTTT GTGCATCAGA TGCTAAAGCA TATGATACAG
    5890       5900       5910       5920       5930       5940
AGGTACATAA TGTTTGGGCC ACACATGCCT GTGTACCCAC AGACCCCAAC CCACAAGAAG
    5950       5960       5970       5980       5990       6000
TAGTATTGGT AAATGTGACA GAAAATTTTA ACATGTGGAA AAATGACATG GTAGAACAGA
    6010       6020       6030       6040       6050       6060
TGCATGAGGA TATAATCAGT TTATGGGATC AAAGCCTAAA GCCATGTGTA AAATTAACCC
    6070       6080       6090       6100       6110       6120
CACTCTGTGT TAGTTTAAAG TGCACTGATT TGGGGAATGC TACTAATACC AATAGTAGTA
    6130       6140       6150       6160       6170       6180
```

FIG. 23

```
ATACCAATAG TAGTAGCGGG GAAATGATGA TGGAGAAAGG AGAGATAAAA AACTGCTCTT
   6190       6200       6210       6220       6230       6240
TCAATATCAG CACAAGCATA AGAGGTAAGG TGCAGAAAGA ATATGCATTT TTTTATAAAC
   6250       6260       6270       6280       6290       6300
TTGATATAAT ACCAATAGAT AATGATACTA CCAGCTATAC GTTGACAAGT TGTAACACCT
   6310       6320       6330       6340       6350       6360
CAGTCATTAC ACAGGCCTGT CCAAAGGTAT CCTTTGAGCC AATTCCCATA CATTATTGTG
   6370       6380       6390       6400       6410       6420
CCCCGGCTGG TTTTGCGATT CTAAAATGTA ATAATAAGAC GTTCAATGGA ACAGGACCAT
   6430       6440       6450       6460       6470       6480
GTACAAATGT CAGCACAGTA CAATGTACAC ATGGAATTAG GCCAGTAGTA TCAACTCAAC
   6490       6500       6510       6520       6530       6540
TGCTGTTGAA TGGCAGTCTA GCAGAAGAAG AGGTAGTAAT TAGATCTGCC AATTTCACAG
   6550       6560       6570       6580       6590       6600
ACAATGCTAA AACCATAATA GTACAGCTGA ACCAATCTGT AGAAATTAAT TGTACAAGAC
   6610       6620       6630       6640       6650       6660
CCAACAACAA TACAAGAAAA AGTATCCGTA TCCAGAGGGG ACCAGGGAGA GCATTTGTTA
   6670       6680       6690       6700       6710       6720
CAATAGGAAA AATAGGAAAT ATGAGACAAG CACATTGTAA CATTAGTAGA GCAAAATGGA
   6730       6740       6750       6760       6770       6780
ATGCCACTTT AAAACAGATA GCTAGCAAAT TAAGAGAACA ATTTGGAAAT AATAAAACAA
   6790       6800       6810       6820       6830       6840
TAATCTTTAA GCAATCCTCA GGAGGGGACC CAGAAATTGT AACGCACAGT TTTAATTGTG
   6850       6860       6870       6880       6890       6900
GAGGGGAATT TTTCTACTGT AATTCAACAC AACTGTTTAA TAGTACTTGG TTTAATAGTA
   6910       6920       6930       6940       6950       6960
CTTGGAGTAC TGAAGGGTCA AATAACACTG AAGGAAGTGA CACAATCACA CTCCCATGCA
   6970       6980       6990       7000       7010       7020
GAATAAAACA ATTTATAAAC ATGTGGCAGG AAGTAGGAAA AGCAATGTAT GCCCCTCCCA
   7030       7040       7050       7060       7070       7080
TCAGCGGACA AATTAGATGT TCATCAAATA TTACAGGGCT GCTATTAACA AGAGATGGTG
   7090       7100       7110       7120       7130       7140
GTAATAACAA CAATGGGTCC GAGATCTTCA GACCTGGAGG AGGAGATATG AGGGACAATT
   7150       7160       7170       7180       7190       7200
GGAGAAGTGA ATTATATAAA TATAAAGTAG TAAAAATTGA ACCATTAGGA GTAGCACCCA
   7210       7220       7230       7240       7250       7260
CCAAGGCAAA GAGAAGAGTG GTGCAGAGAG AAAAAAGAGC AGTGGGAATA GGAGCTTTGT
   7270       7280       7290       7300       7310       7320
TCCTTGGGTT CTTGGGAGCA GCAGGAAGCA CTATGGGCGC ACGGTCAATG ACGCTGACGG
   7390       7340       7350       7360       7370       7380
TACAGGCCAG ACAATTATTG TCTGGTATAG TGCAGCAGCA GAACAATTTG CTGAGGGCTA
   7390       7400       7410       7420       7430       7440
```

*FIG. 24*

```
TTGAGGCGCA ACAGCATCTG TTGCAACTCA CAGTCTGGGG CATCAAGCAG CTCCAGGCAA
    7450       7460       7470       7480       7490       7500
GAATCCTGGC TGTGGAAAGA TACCTAAAGG ATCAACAGCT CCTGGGGATT TGGGGTTGCT
    7510       7520       7530       7540       7550       7560
CTGGAAAACT CATTTGCACC ACTGCTGTGC CTTGGAATGC TAGTTGGAGT AATAAATCTC
    7570       7580       7590       7600       7610       7620
TGGAACAGAT TTGGAATAAC ATGACCTGGA TGGAGTGGGA CAGAGAAATT AACAATTACA
    7630       7640       7650       7660       7670       7680
CAAGCTTAAT ACATTCCTTA ATTGAAGAAT CGCAAAACCA GCAAGAAAAG AATGAACAAG
    7690       7700       7710       7720       7730       7740
AATTATTGGA ATTAGATAAA TGGGCAAGTT TGTGGAATTG GTTTAACATA ACAAATTGGC
    7750       7760       7770       7780       7790       7800
TGTGGTATAT AAAAATATTC ATAATGATAG TAGGAGGCTT GCTAGGTTTA AGAATAGTTT
    7810       7800       7810       7820       7830       7840
TTGCTGTACT TTCTATAGTG AATAGAGTTA GGCAGGGATA TTCACCATTA TCGTTTCAGA
    7870       7880       7890       7900       7910       7920
CCCACCTCCC AACCCCGAGG GGACCCGACA GGCCCGAAGG AATAGAAGAA GAAGGTGGAG
    7930       7940       7950       7960       7970       7980
AGAGAGACAG AGACAGATCC ATTCGATTAG TGAACGGATC CTTAGCACTT ATCTGGGACG
    7990       8000       8010       8020       8030       8040
ATCTGCGGAG CCTTGTGCCT CTTCAGCTAC CACCGCTTGA GAGACTTACT CTTGATTGTA
    8050       8060       8070       8080       8090       8100
ACGAGGATTG TGGAACTTCT GGGACGCAGG GGGTGGAAG CCCTCAAATA TTGGTGGAAT
    8110       8120       8130       8140       8150       8160
CTCCTACAGT ATTGGAGTCA GGAACTAAAG AATAGTGCTG TTAGCTTGCT CAATGCCACA
    8170       8180       8190       8200       8210       8220
GCCATAGCAG TAGCTGAGGG GACAGATAGG GTTATAGAAG TAGTACAAGG AGCTTGTAGA
    8230       8240       8250       8260       8270       8280
GCTATTCGCC ACATACCTAG AAGAATAAGA CAGGGCTTGG AAAGGATTTT GCTATAAGAT
    8290       8300       8310       8320       8330       8340
GGGTGGCAAG TGGTCAAAAA GTAGTGTGGT TGGATGGCCT ACTGTAAGGG AAAGAATGAG
    8350       8360       8370       8380       8390       8400
ACGAGCTGAG CCAGCAGCAG ATGGGGTGGG AGCAGCATCT CGAGACCTGG AAAAACATGG
    8410       8420       8430       8440       8450       8460
AGCAATCACA AGTAGCAATA CAGCAGCTAC CAATGCTGCT TGTGCCTGGC TAGAAGCACA
    8470       8480       8490       8500       8510       8520
AGAGGAGGAG GAGGTGGGTT TTCCAGTCAC ACCTCAGGTA CCTTTAAGAC CAATGACTTA
    8530       8540       8550       8560       8570       8580
CAAGGCAGCT GTAGATCTTA GCCACTTTTT AAAAGAAAAG GGGGGACTGG AAGGGCTAAT
    8590       8600       8610       8620       8630       8640
TCACTCCCAA CGAAGACAAG ATATCCTTGA TCTGTGGATC TACCACACAC AAGGCTACTT
    8650       8660       8670       8680       8690       8700
```

*FIG. 25*

```
CCCTGATTGG CAGAACTACA CACCAGGGCC AGGGGTCAGA TATCCACTGA CCTTTGGATG
      8710       8720       8730       8740       8750       8760
GTGCTACAAG CTAGTACCAG TTGAGCCAGA TAAGGTAGAA GAGGCCAATA AAGGAGAGAA
      8770       8780       8790       8800       8810       8820
CACCAGCTTG TTACACCCTG TGAGCCTGCA TGGAATGGAT GACCCTGAGA GAGAAGTGTT
      8830       8840       8850       8860       8870       8880
AGAGTGGAGG TTTGACAGCC GCCTAGCATT TCATCACGTG GCCCGAGAGC TGCATCCGGA
      8890       8900       8910       8920       8930       8940
GTACTTCAAG AACTGCTGAC ATCGAGCTTG CTACAAGGGA CTTTCCGCTG GGGACTTTCC
      8950       8960       8970       8980       8990       9000
AGGGAGGCGT GGCCTGGGCG GAACTGGGGA GTGGCGAGCC CTCAGATGCT GCATATAAGC
      9010       9020       9030       9040       9050       9060
AGCTGCTTTT TGCCTGTACT GGGTCTCTCT GGTTAGACCA GATTTGAGCC TGGGAGCTCT
      9070       9080       9090       9100       9110       9120
CTGGCTAACT AGGGAACCCA CTGCTTAAGC CTCAATAAAG CTT
```

FIG. 26

NUCLEIC ACID PROBE OF HUMAN IMMUNODEFICIENCY VIRUS TYPE 1 (HIV-1), AND A METHOD AND KIT EMPLOYING THIS PROBE FOR DETECTING THE PRESENCE OF NUCLEIC ACID OF HIV-1

CROSS-REFERENCE TO RELATED APPLICATIONS

This is a continuation of application Ser. No. 07/158,652, filed Feb. 22, 1988 (pending), which is a division of application Ser. No. 06/771,248, filed Aug. 30, 1985 (now abandoned). This application is also a continuation-in-part of application Ser. No. 07/999,410, filed Dec. 31, 1992 (pending), which is a continuation of application Ser. No. 07/499,210 filed Mar. 19, 1990 (pending), which is a continuation of application Ser. No. 06/771,230, filed Aug. 30, 1985 (now abandoned), which is a continuation-in-part of application Ser. No. 06/706,562, filed Feb. 28, 1985 (now abandoned), which is a continuation-in-part of application Ser. No. 06/558,109, filed Dec. 5, 1983 (now abandoned).

BACKGROUND OF THE INVENTION

The invention relates to cloned DNA sequences indistinguishable from genomic RNA and DNA of lymphadenopathy-associated virus (LAV), a process for their preparation and their uses. It relates more particularly to stable probes including a DNA sequence which can be used for the detection of the LAV virus or related viruses or DNA proviruses in any medium, particularly biological samples containing, any of them. The invention also relates to polypeptides, whether glycosylated or not, encoded by said DNA sequences.

Lymphadenopathy-associated virus (LAV) is a human retrovirus first isolated from the lymph node of a homosexual patient with lymphadenopathy syndrome, frequently a prodrome or a benign form of acquired immune deficiency syndrome (AIDS). Subsequently, other LAV isolates have been recovered from patients with AIDS or pre-AIDS. All available data are consistent with the virus being the causative agent of AIDS.

A method for cloning such DNA sequences has already been disclosed in British Patent Application Nr. 84 23659 filed on Sep. 19, 1984. Reference is hereafter made to that application as concerns subject matter in common with the further improvements to the invention disclosed herein.

Application Nr. 84 23659 Filed on Sep. 19, 1984

The text of British Patent Application Number 84 23659, filed on Sep. 19, 1984, is as follows:

Cloned DNA Sequences, Hybridizable with Genomic RNA of Lymphadenopathy-Associated Virus (LAV)

The invention relates to cloned DNA sequences hybridizable to genomic RNA and DNA of lymphadenopathy-associated virus (LAV), a process for their preparation and their uses. It relates more particularly to stable probes including a DNA sequence which can be used for the detection of the LAV virus or related viruses or DNA pro-viruses in any medium, particularly biological, samples containing of any them.

Lymphadenopathy-associated virus (LAV) is a human retrovirus first isolated from the lymph node of a homosexual patient with lymphadenopathy syndrome, frequently a prodrome or a benign form of acquired immune deficiency syndrome (AIDS) (cf. 1). Subsequently other LAV isolates have been recovered from patients with AIDS or pre-AIDS (Cf. 2-5). All available data are consistent with the virus being the causative agent of AIDS (cf. 11).

The virus is propagated on activated T lymphocytes and has a tropism for the T-cell subset OKT4 (cf. 2-6), in which it induces a cytopathic effect. However, it has been adapted for growth in some Epstein-Barr virus transformed B-cell lines (cf. 7), as well as in the established T-lymphoblastic cell line, CEM.

LAV-like viruses have more recently been independently isolated from patients with AIDS and pre-AIDS. These viruses called HTLV-III (Human T-cell Leukemia/Lymphoma virus type III (cf. 12-15) and ARV (AIDS-associated retrovirus) seem to have many characteristics similar to those of LAV and it is thus probable that they represent independent isolates of the LAV prototype.

Detection methods so far available are based on the recognition of core proteins. Such a method is disclosed in European application titled "Antigènes, moyens et méthode pour le diagnostic de lymphadénopathie et du syndrome d'immunodépression acquise" filed on Sep. 14, 1984, under the priority of British application Serial Nr. 83 24800 filed on Sep. 15, 1983. As a matter of fact, a high prevalence of anti-p25 antibodies has been found in the sera of AIDS and pre-AIDS patients and to a lower but significant extent in the high-risk groups for AIDS (cf. 8-10). However the same sera were found not to recognize the virus as a whole, in a non-disintegrated state.

The present invention aims at providing new means which should not only also be useful for the detection of LAV or related viruses (hereafter more generally referred to as "LAV viruses"), but also have more versatility, particularly in detecting specific parts of the genomic DNA of said viruses whose expression products are not always detectable by immunological methods.

The DNAs according to the invention consist of DNAs which contain DNA fragments, hybridizable with the genomic RNA of LAV. Particularly said DNAs consist of said cDNAs or cDNA fragments or of recombinant DNAs containing said cDNAs or cDNA fragments.

Preferred cloned cDNA fragments respectively contain the following restriction sites in the respective orders which follow (from the 3' end to the 5' end):
  1) HindIII, SacI, BglII (LAV75)
  2) HindIII, SacI, BglII, BglII, KpnI (LAV82)
  3) HindIII, SacI, BglII, BglII, KpnI, XhoI, BamHI, HindIII, BglII (LAV13).

The LAV75, LAV82, and LAV13 designations correspond to the designations of the recombinant plasmids designated as pLAV 75, pLAV 82 and pLAV 13, respectively, in which they were first cloned. In other words, LAV 75, LAV 82, and LAV 13 respectively present as inserts in said recombinant plasmids. For convenience, the designations LAV 75, LAV 82 and LAV 13 will be further used throughout this specification to designate the cDNA fragments, whether the latter are in isolated form or in a plasmid forms, whereby the other DNA parts of said last mentioned recombinants are identical to or different from the corresponding parts of pLAV 75, pLAV 82, and pLAV 13, respectively.

Preferred cDNAs also (like LAV 75, LAV 82, and LAV 13) contain a region corresponding to the R and U 3 regions of the LTR (Long Terminal Repeat) as well as the 3' end of the coding region of the retroviral DNA. Particularly, if it is assumed that the retroviral structure of LAV is in general agreement with the retroviral genomic structures to date.

LAV 13, which has a size of about 2.5 Kbp has been found of particular advantage. It is highly specific of LAV or LAV related viruses and does also recognizes more of the LAV retroviral genomes than do LAV75 or LAV82. Particularly, LAV 13 enabled the identification of the RU 5 junction of the retroviral genomes within the LTR and, subsequently, the sizes of the LAV genomes, which average from about 9.1 to about 9.2 kb.

LAV 13 is free of restriction sites for the following enzymes Eco RI, Nru I, Pvu I, Sal I, Sma I, Sph I, Stu I, and Xba I.

LAV 13 further appears to contain at least part of the DNA sequences corresponding to those which, in retroviral genomes, code for the envelope protein.

The invention further relates to any of the fragments contained in the cDNA, which seems to correspond to part of the whole of the LAV retroviral genome, which is characterized by a series of restriction sites in the order hereafter (from the 5' end to the 3' end).

The coordinates of the successive sites of the whole LAV genome (restriction map) are indicated hereafter too, with respect to the Hind III site (selected as of coordinate 1), which is located in the R region. The coordinates are estimated to within ±200 bp. Some coordinates are better established than others.

| | |
|---|---|
| Hind III | 0 |
| Sac I | 50 |
| Bam HI | 460 |
| Hind III | 520 |
| Bam HI | 600 |
| Pst I | 800 |
| Hind III | 1100 |
| Bgl II | 1500 |
| Kpn I | 3500 |
| Kpn I | 3900 |
| Eco RI | 4100 |
| Eco RI | 5300 |
| Sal I | 5500 |
| Kpn I | 6100 |
| Bgl II | 6500 |
| Bgl II | 7600 |
| Hind III | 7850 |
| Bam HI | 8150 |
| Xho I | 8600 |
| Kpn I | 8700 |
| Bgl II | 8750 |
| Bgl II | 9150 |
| Sac I | 9200 |
| Hind III | 9250 |

The abovesaid DNA according to the invention optionally contains an additional Hind III approximately at the 5 550 coordinate.

The invention further relates to other preferred DNA fragments corresponding substantially to those which in relation to the abovesaid restriction map extend respectively:
from approximately Kpn I (6 100) to approximately Bgl II (9150), said fragment being thought to correspond at least in part to the gene coding for the proteins of the envelope; in particular a protein p110 of about 110,000 Daltons is encoded by this region;
from approximately Kpn I (3 500) to approximately Bgl II (6500), said fragment being thought to correspond at least in part to the pol gene, coding for the virus polymerase;
from approximately Pst (800) to approximately Kpn I (3500), said fragment being thought to correspond at least in part to the gag gene, which codes for the core antigens, including the p25, the p18, and the p13 proteins.

More particularly, the invention relates to any fragment corresponding to the above ones, having substantially the same sites at substantially same distances from one another, all of these fragments having in common the capability of hybridizing with the LAV retroviral genomes. It is of course understood that fragments which would include some deletions or mutation which would not substantially alter their capability of also hybridizing with the LAV retroviral genomes are to be considered as forming obvious equivalents of the DNA fragments more specifically referred to hereabove.

Additional features of the invention will appear in the course of the disclosure of additional features of preferred DNAs of the invention, the preparation conditions and the properties of which will be illustrated hereafter in a non limitative manner. Reference will also be had to the drawings in which:

FIG. 27 shows restriction maps of preferred LAV inserts contained in plasmid recombinants;

FIG. 28 shows restriction maps of complete LAV fragments.

1. Construction of a cDNA Library 1.1 Virus Purification

Virions were purified from FR8, an immortalized, permanent LAV producing B-Lymphocyte line (cf. 7) (deposited at the "Collection Nationale de Cultures de Micro-organismes" of the INSTITUT PASTEUR of Paris, under Nr. 1-303 on May 9, 1984). The purification protocol was described (cf. 1). The main steps were:
polyethylene-glycol treatment of culture supernatant, pelleting through % sucrose cushion, banding on 20-60% sucrose gradient and pelleting of the virus-containing fractions.

1.2 First-Strand cDNA Synthesis

The virus associated detergent activated endogenous reaction is a technique bringing into play the reverse transcriptase of the virus, after purification thereof and lysis of its envelope.

For each reaction, purified virus corresponding to 250-300 ml of FR8 supernatant was used. Final reaction volume was 1 ml. Incubation was at 37° C. for 45 nm. Protein concentration was about 250 microg/ml. Buffer was: NaCl 25 mM; Tris HCl pH 7.8 50 mM, dithiothreitol 10 mM, $MgCl_2$ 6 mM, each of dATP, dGTP, dTTP at 0.1 mM, Triton X-100 0.02%; oligo dT primer 50 microg/ml. The cDNA was labelled 15 nm with alpha $^{32}$P-dCTP 400 Ci/mmole to 0.6 microM plus cold dCTP to 4 microM. Afterwards, cold dCTP was added to 25 microM to ensure optimal elongation of the first strand.

The reaction was stopped 30 nm after the dCTP chase by adding EDTA to 20 mM, SDS to 0.5%, digesting one hour with proteinase K at 100 microg/ml and phenol-chloroform extraction.

cDNA was then purified on G-50 Sephadex (Pharmacia) and ethanol precipitated.

1.3 2nd Strand Synthesis and Cloning

Purified cDNA-RNA hybrids were treated with DNA polymerase I and RNase H, according to GUBLER and HOFFMAN (cf. 17). Double-stranded cDNA was dC-tailed with terminal transferase and annealed to dG-tailed Pst-digested pBR 327 (cf. 34) a derivative of pBR 322.

A cDNA library was obtained by transfection of *E. coli* C 600 recBc strain.

2. Detection of LAV-Specific Clones

2.1 Screening of the Library recombinant clones were grown on nitrocellulose filters and in situ colony hybridization (cf. 35) was performed with another batch of cDNA made in endogenous virus-associated reaction as described (cf. 1.2) and labelled with $^{32}$P. About 10% of the clones could be detected.

A major family was obtained by small-scale amplification of these clones and cross-hybridization of their inserts. Among these clones a major family of hybridizing recombinants was identified. Three of these cDNA clones, named pLAV 13, 75 and 82, carrying inserts of 2.5, 0.6, and 0.8 kb respectively were further characterized (FIG. 27).

All three inserts have a common restriction pattern at one end, indicating a common priming site. The 50 bp long common Hind III-Pst I fragment was sequenced (FIG. 27) and shown to contain a polyA stretch preceding the cloning dC tail. The clones are thus copies of the 3' end of a polyA-RNA.

The LAV 13 specificity was shown by different assays.

The specificity of pLAV 13 was determined in a series of filter hybridization experiments using nick-translated pLAV 13 as a probe. Firstly, the probe hybridized to purified LAV genomic RNA by dot and Northern blotting (data not shown). pLAV 13 also hybridizes to the genomic RNA of virus concentrated from culture supernatant directly immobilized on filters (dot blot technique). LAV RNA from different sources: normal T-cells, FR8 and other B-cell LAV producing lines, CEM cells and, although less strongly, LAV from the bone marrow culture from a haemophiliac with AIDS (cf. 3) were detected in a similar manner. Uninfected cultures proved negative. This rapid dot blot technique can be adapted with minor modifications to the detection of LAV in serum or other body fluids.

Secondly, the probe detected DNA in the Southern blots of LAV-infected T-lymphocytes and in the LAV-producing CEM cell line. No hybridization was detected in the DNA of uninfected lymphocytes nor in the DNA from normal liver (data not shown) under the same hybridization conditions.

A third characteristic resulted from the possibility of using LAV 13 to identify the whole retroviral genome of the LAV viruses as disclosed hereafter. Particularly characteristic 1.45 kb Hind III fragment which co-migrates with an internal viral fragment in Hind III cleaved pLAV 13 was detected. Bands at 2.3 and 6.7 kb were also detected. As the probe was only 2.5 kb long and as no junction fragments could be detected, it is probable that these extra-bands represent internal fragments arising from a Hind III polymorphism of the LAV genome.

Together, these data show that pLAV 13 DNA is exogenous to the human genome and detects both RNA and integrated DNA forms derived from LAV infected cells. Thus, pLAV 13 is LAV specific. Being oligo-dt primed, pLAV 13 must contain the R and U3 regions of the LTR as well as the 3' end of the coding region, assuming a conventional retroviral genome structure.

Cloning of LAV Genomic DNA

Having found a HindIII site within the R region of the LTR, it was decided to clone the LAV genome by making a partial Hind III digest of proviral DNA from LAV infected cells. It was found that: (a) partial digestion increased the chance of isolating complete clones and (b) Hind III fragments were easily cloned in lambda replacement vectors. The DNA isolated from T-cells of a healthy donor after in vitro infection with LAV was partially digested with Hind III and fractionated. A 9$^+$ 1.5 kb DNA containing fraction was precipitated and ligated into the Hind III arms of lambda-L47.1 (cf. 18).

The cloning of LAV genomic DNA was carried out more particularly as follows:

cDNAs was prepared from LAV infected T cells as described above, then partially digested with Hind III and fractionated on a 5-40% sucrose gradient in 10 mM Tris.Cl pH 8. 10 mM EDTA, 1 M NaCl (SW41 rotor, 16 hours at 40 000 rpm). A single fraction (9±0.5 kb) was precipitated with 20 microg/ml Dextran T40 as carrier and taken up in TE-buffer (10 mM Tris.Cl pH 8, 1 mM EDTA). Lambda-L47.1 Hind III arms were prepared by first ligating the cos sites followed by Hind III digestion and fractionation through a 5-40% sucrose gradient. Fractions containing only the lambda-Hind III arms were pooled, precipitated and taken up in TE-buffer. Ligation of arms to DNA was made at approximately 200 microg DNA/ml using a 3:1 molar excess of arms and 300 units of T4 DNA ligase (Biolabs). In vitro packaging lysates were made according to (38). After in vitro packaging the phage lysate was plated out on NM538 on a C600 recBC strain. Approximately two million plaques were screened by in situ hybridization (cf. 39) using nitrocellulose filters. Hybridization was performed at 68° C. in 1×Denhardt solution, 0.5% SDS, 2×SSC, 2 mM EDTA. Probe: $^{32}$P nick-translated LAV insert of pLAV 13 at >108 cpm/microg: Filters were washed 2×30 minutes in 0-1 SSC, 0.1% SDS at 68° C., and exposed to Kodak XAR-5 film for 29-40 hours. Seven positive clones were identified and plaque purified on a C 600 rec BC strain. Liquid cultures were grown and the recombinant phages banded in CsCl. Plage DNA was extracted and digested under the appropriate conditions.

Seven independent clones were so derived from approximatively two million phage plaques after screening in situ with a nick-translated pLAV 13 insert as a probe. Restriction maps of lambda-J19 as well as of a Hind III polymorph lambda-J81 are shown in FIG. 28. Other recombinants lambda-J27, lambda-J31 and lambda-J57 had the same Hind III map as lambda-J19. The map of lambda-J81 is identical but for an additional Hind III site at coordinate of approximately 5 550.

The restriction maps of FIG. 28 were oriented by hybridizing blots with respect to pLAV 13 DNA.

The restriction map of the LAV 13 cDNA clone is also shown in FIG. 28. The restriction sites of lambda-J19 are: B-Bam HI, Bg-Bgl II, H-Hind III, K-Kpn I, P-Pst I, R-Eco RI, S-Sac I, Sa-Sal-I, and X-Xho I. Underneath the scale is a schema for the general structure of the retroviruses showing the LTR elements U3, R and U5. Only the R/US boundary has been defined and other boundaries are only drawn figuratively.

There may be other Bam HI sites in the 5' 0.52 kb Hind III fragment of lambda-J19. They generate fragments that are too small to be detected.

FIG. 28 also shows those Hind III fragments of lambda-J19 and lambda-J81 which are detected by pLAV 13 (marked (+)), those which are not detected (−).

More particularly lambda-319 shows four Hind III bands of 6.7, 1.45, 0.6, and 0.52 kb the first two of which correspond to bands in the genomic blot of Hind III restricted DNA. The smallest bands of 0.6 and 0.52 kb were not seen in the genomic blot but the fact that they appear in all the independently derived clones analyzed indicates that they represent internal and not junction fragments, assuming a random integration of LAV proviral DNA. Indeed, the 0.5 kb band hybridizes with pLAV 13 DNA (FIG. 28) through the small Hind III-Pst I fragment of pLAV 13. Thus the 0.5 kb Hind III fragment of lambda-J19 contains the R-U5 junction within the LTR.

It appears that lambda-J81 is a restriction site polymorph of lambda-J19. Lambda-J81 shows five Hind III bands of 4.3, 2.3, 1.45, 0.6, and 0.52 kb. The 2.3 kb band is readily detected in the genomic blot by a pLAV 13 probe, but not the 4.3 kb fragment. That lambda-J81 is a Hind III polymorph and not a recombinant virus is shown by the fact that nick-translated lambda-J19 DNA hybridizes to all five Hind III bands of lambda-J81 under stringent hybridization and washing conditions. Also other restrictions sites in lambda-J81 are identical to those of lambda-J19.

Relationship to Other Human Retroviruses

HTLV-I and HTLV-II constitute a pair of C-type transforming retroviruses with a tropism for the T-cell subset, OKT4 (cf. 20). An isolate of HTLV-I has been totally sequenced (cf. 21) and partial sequencing of an HTLV-II has been reported (cf. 22-24). Both genomes (one LTR) were approximately 8.3 kb in length, have a pX region and show extensive sequence homology. They hybridize between themselves under reasonably stringent conditions (40% formamide, 5×SSC) and even at 60% formamide the pX regions hybridize (cf. 26). Thus a conserved pX region is a hallmark of this class of virus.

We have compared cloned LAV DNA and cloned HTLV-II DNA (pMO (cf. 27)) by blot-hybridization and found no cross-hybridization under low stringency conditions of hybridization and washing. For example, Hind III digested lambda-J19, lambda-J27 and lambda-J81 were electrophoresed, blotted and hybridized overnight with $^{32}$P nick-translated pMO (HTLV-II) DNA (having a specific activity greater than $0.5 \times 10^8$ cpm/microg) in 20% formamide, 5×SSC, 1×Denhardt's solution, 10% Dextran sulphate, at 37° C. Filters were washed at 37° C. ($t_m$-50) $t_m$-50 using a 53.1% GC content derived from the HTLV-I sequence (21). The washings were repeated at 50° C. and 65° C. in 1×SSX, 0.1% SDS. Even when hybridized in 20% formamide, 8×SSC ($t_m$-50) and washed at 37° C. in 2×SSC ($t_m$-50) no hybridization was detected after two days exposure at −70° C. using an intensifying screen.

Thus, there is no molecular evidence of a relationship between LAV and the HTLV viruses. In addition, the LAV genome is approximately 9 kb long in contrast to 8.3 kb for the HTLV viruses. Despite their comparable genome sizes LAV and Visna (cf. 29) cloned viral genomes do not cross-hybridize, nor does LAV with a number of human endogenous viral genomes (cf. 30) under non stringent conditions (hybridization—20% formamide, 8 SSC, 37° C.; washing—2 SSC, 0.1% SDS, 37° C.

The invention also relates more specifically to cloned probes which can be made starting from any DNA fragment according to the invention, thus to recombinant DNAs containing such fragments, particularly any plasmids amplifiable in procaryotic or eucaryotic cells and carrying said fragments. As mentioned earlier a preferred DNA fragment is LAV 13.

Using the cloned provirus DNA as a molecular hybridization probe—either by marking with radionucleotides or with fluorescent reagents—LAV virion RNA may be detected directly in the blood, body fluids and blood products (e.g. of the antihemophylic factors such as Factor VIII concentrates) and vaccines, i.e. hepatitis B vaccine. It has already been shown that whole virus can be detected in culture supernatants of LAV producing cells. A suitable method for achieving that detection comprises immobilizing virus onto said a support e.g. nitrocellulose filters, etc., disrupting the virion and hybridizing with labelled (radiolabelled or "cold" fluorescent- or enzyme-labelled) probes. Such an approach has already been developed for Hepatitis B virus in peripheral blood (according to SCOTTO J. et al. Hepatology (1983), 3, 379-384).

Probes according to the invention can also be used for rapid screening of genomic DNA derived from the tissue of patients with LAV related symptoms, to see if the proviral DNA or RNA is present in host tissue and other tissues.

A method which can be used for such screening comprise the following steps: extraction of DNA from tissue, restriction enzyme cleavage of said DNA, electrophoresis of the fragments and Southern blotting of genomic DNA from tissues, subsequent hybridization with labelled cloned LAV provival DNA. Hybridization in situ can also be used.

Lymphatic fluids and tissues and other non-lymphatic tissues of humans, primates and other mammalian species can also be screened to see if other evolutionary related retrovirus exist. The methods referred to hereabove can be used, although hybridization and washings would be done under non stringent conditions.

The DNA according to the invention can be used also for achieving the expression of LAV viral antigens for diagnostic purposes as well as far the production of a vaccine against LAV. Of particular advantage in that respect are the DNA fragments coding core (gag region) and for envelope proteins, particularly the DNA fragment extending from Kpn I (6 100) to BglII(9 150).

The methods which can be used are multifold:
a) DNA can be transfected into mammalian cells with appropriate selection markers by a variety of techniques, calcium phosphate precipitation, polyethylene glycol, protoplast-fusion, etc.
b) DNA fragments corresponding to genes can be cloned into expression vectors for E. coli, yeast- or mammalian cells and the resultant proteins purified.
c) The proviral DNA can be "shot-gunned" (fragmented) into procaryotic expression vectors to generate fusion polypeptides. Recombinant producing antigenically competent fusion proteins can be identified by simply screening the recombinants with antibodies against LAV antigens
d) The invention also relates to oligopeptides deduced from the DNA sequence of LAV antigen-genes to produce immunogens and antigens and which can be synthesized chemically.

All of the above (a-d) can be used in diagnostics as sources of immunogens or antigens free of viral particles, produced using non-permissive systems, and thus of little or no biohazard risk.

The invention further relates to the hosts (procaryotic or eucaryotic cells) which are transformed by the above mentioned recombinants and which are capable of expressing said DNA fragments.

Finally, it also relates to vaccine compositions whose active principle is to be constituted by any of the expressed antigens, i.e. whole antigens, fusion polypeptides, or oligopeptides.

The invention finally refers to the purified genomic mRNA, which can either be extracted as such from the LAV viruses or resynthesized back from the cDNA, particularly to a purified mRNA having a size approximating 9.1 to 9.2 kb, hybridizable to any of the DNA fragments defined hereabove or to parts of said purified mRNA. The invention also relates to parts of said RNA. The nucleotidic structures of this purified RNA or of the parts thereof can indeed be deduced from the nucleotidic sequences of the related cDNAs.

It will finally be mentioned that lambda-J19 and lambda-J81 have been deposited at the Collection Nationale des Cultures de Micro-organismes (C.N.C.M.) of the INSTITUT PASTEUR of Pasteur (France) under Nr. 1-338 and 1-339, respectively, on Sep. 11, 1984.

The invention finally refers to the genomic DNA, the DNA sequence of which can be determined and used to predict the amino acid sequences of the viral protein (antigens) and to the RNA probes which can be derived from the cDNA.

There follows the bibliography to which references have been made throughout this specification by bracketed numbers.

All the publications referred to in this bibliography are incorporated herein by reference.

REFERENCES

1. Barré-Sinoussi, F. et al. Science, 220, 868-871 (1983).
2. Montagnier, L. et al. in Human T-cell Leukemia Viruses (eds. R. C. Gallo, M. Essex and L. Gross) p. 363-379 (Cold Spring Harbor, New-York, 1984).
3. Vilmer, E. et al. Lancet, ii, 753-757 (1984).
4. Ellrodt, A. et al. Lancet, 1, 1383-1385 (1984).
5. Feorino, M. P. et al. Science, 225, 69-72 (1984).
6. Klatzmann, D. et al. Science, 225, 59-63 (1984).
7. Montagnier, L. et al. Science, 885, 63-66 (1984).
8. Brun-Vézinet, F. et al. Lancet, 1, 1253-1256 (1984).
9. Kalyanaraman, V. S. et al. Science, 225, 321-323 (1984).
10. Brun-Vézinet, F. et al. Science in Press.
11. Montagnier, L., Barre-Sinoussi, F. and Chemann, J. C. in Prog. Immunodef. Res. Therapy, I, (eds. C. Griscelli and J. Vossen) p. 367-372 (Excerpta Medica, Amsterdam, 1984).
12. Popovic, M., Sarngadharan, M. G., Read, E. and Gallo, R. C. Science, 224, 497-500 (1984).
13. Gallo, et al. Science, 224, 500-503 (1984).
14. Schupbach, 3. et al. Science, 224, 503-505 (1984).
15. Sarngadharan, M. G., Popovic, M., Bruch, L., Schüpbach, J. and Gallo R. C. Science, 224, 506-508 (1984).
16. Levy, J. A. et al. Science, 225, 840-842 (1984).
17. Gubler, U., and Hoffman, B. J. Gene, 25, 263-269 (1983).
18. Loenen, W. A. M. and Brammar, W. J. Gene, 10, 249-259 (1980).
19. Fujiyama, A. et al. Nuc. Acids Res., 11, 4601-4610 (1983).
20. Gallo, R. C. et al. Proc Natl. Acad. Sci. USA, 79, 5680-5683 (1982).
21. Seiki, M., Hattori, S., Hirayama, Y. and Yoshida, M. Proc. Natl. Acad. Sci. USA, 80, 3618-3622 (1983).
22. Haseltine, W. A. et al. Science, 225, 419-421 (1984).
23. Sodroski, J. et al. Science, 225, 421-424 (1984).
24. Shimotohno, K. et al. Proc. Natl. Acad. Sci. USA, in press.
25. Chen, I. S. Y, Mc Laughlin, J., Gasson, J. C., Clark, S. C. and Golde, D. W. Nature, 305, 502-505 (1983).
26. Shaw, G. M. et al. Proc. Natl. Acad. Sci. USA, 81, 4544-4548 (1984).
27. Gelmann, E. P., Franchini, G., Manzari, V., Wong-Staal, F. and Gallo, R. C. Proc. Natl. Acad. Sci. USA, 81, 993-997 (1984).
28. Arya, S. K. et al. Science, 225, 927-930 (1984).
29. Harris, J. D. et al. Virology, 113, 573-583 (1981).
30. Steele, P. E., Rabson, A. B., Bryan, T. and Martin, M. A. Science, 225, 943-947 (1984).
31. Montagnier, L. et al. Ann. Virol. (Institut Pasteur), 135 E, 119-134 (1984).
32. Lenz, J. et al. Nature, 308, 467-470 (1984).
33. Chen, I. S. Y., Mc Laughlin, J. and Golde, D. W. Nature, 309, 276-279 (1984).
34. Soberon, X., Covarrubias, L. and Bolivar, F. Gene, 9, 287-305 (1980).
35. Grunstein, M. and Hognhess, D. Proc. Natl. Acad. Sci. USA, 72, 3961-3965 (1975).
36. Sanger, F., Nicklen, S, and Coulsen, A. R. Proc. Natl. Acad. Sci. USA, 79, 5463-5476 (1977).
37. Southern, E. M. J. Mol. Biol., 98, 503-517 (1975).
38. Ish-Horowicz, D. and Burke, J. F. Nucl. Acids Res., 9, 2989-2998 (1981).
39. Benton, W. D. and Davis, R. W. Science, 196, 180-182 (1977).

Claims

1. A cloned DNA which contains a DNA which is hybridizable with the genomic RNA of the LAV, viruses or a fragment of said hybridizable DNA.
2. The DNA of claim 1 which is a recombinant of said hybridizable DNA or DNA fragment hybridizable with the genomic RNA of the LAV virus.
3. The DNA of claim 1 or 2 wherein said hybridizable DNA or DNA fragment is a cDNA.
4. The DNA of claims 1 to 3 which contains the following restriction sites in the—following order (from the 3' end to the 5' end): Hind III, Sac I, Bgl II (LAV 75).
5. The DNA of claim 4 which contains the following restriction sites in the following order: Hind III, Sac I, Bgl II, Bgl II, Kpn I (LAV 82).
6. The DNA of claim 4 which contains the following restriction sites in the following order: Hind III, Sac I, Bgl II, Bgl II, Kpn I, XHo I, Bam HI, Hind III, 891 II (LAV 13)
7. The DNA of claim 6 which has a size of about 2.5 kb.
8. The DNA of any of claims 1 to 7 which contains a region corresponding to the R and U3 regions of the LTR as well as to the 3' end of the coding region of the retroviral DNA.
9. The DNA of claim 1 which has a size from about 9.1 to 9.2 kb.
10. The DNA of claim 9 which contains the following series of restriction sites:

| | |
|---|---|
| Hind III | 0 |
| Sac I | 50 |
| Barn HI | 460 |
| Hind III | 520 |
| Barn HI | 600 |
| Pst I | 800 |
| Hind III | 1100 |
| Bgl II | 1500 |
| Kpn 1 | 3500 |
| Kpn I | 3900 |
| Eco RI | 4100 |
| Eco RI | 5300 |
| Sal I | 5500 |
| Kpn I | 6100 |
| Bgl II | 6500 |
| Bgl III | 7600 |
| Hind III | 7850 |
| Bam HI | 8150 |
| Xho I | 8600 |
| Kpn I | 8700 |
| Bgl I | 8750 |
| Bgl I | 9150 |
| Sac I | 9200 |
| Hind III | 9250 |

11. The DNA of claim 10 which contains an additional Hind III approximately at the 5 550 coordinate.
12. A DNA fragment according to claim 1 which comprises a sequence extending from approximately Kpn I (6100) to approximately Bam HI (8150) of the sequence defined in claim 11.
13. A DNA fragment according to claim 1 which comprises a sequence extending from approximately Kpn I (3500) to approximately Bgl II (6500) of the sequence defined in claim 11

14. A DNA fragment according to claim 1 which comprises a sequence extending from approximately Pst (800) to approximately Kpn 1 (3500) of the sequence defined in claim 11.

15. A DNA fragment of claim 1 which codes for the envelope proteins.

16. A DNA fragment of claim 1 which codes for the retroviral polymerase.

17. A DNA fragment which codes for the core proteins.

18. A probe for the in vitro detection of LAV which consists of a DNA according to any of claims 1 to 17.

19. An expression vector, particularly a plasmid, for the transformation of procaryotic or eucaryotic cells which contains an insert consisting of a DNA fragment hybridizable with the retroviral genome of LAV viruses as defined in any of claims 1 to 17.

20. The vector of claim 18 which contains the DNA fragment of claim

21. A microorganism, eukaryotic or prokaryotic cell which is transformed by a vector according to claim 19 or 20 and which expresses the polypeptide encoded by the corresponding DNA fragment.

22. The purified RNAs of LAV viruses which have sizes from 9.1 to 9.2

BRIEF SUMMARY OF THE INVENTION

The present invention aims at providing additional new means which should not only also be useful for the detection of LAV or related viruses (hereafter more generally referred to as "LAV viruses"), but also have more versatility, particularly in detecting specific parts of the genomic DNA of said viruses whose expression products are not always directly detectable by immunological methods.

The present invention further aims at providing polypeptides containing sequences in common with polypeptides encoded by the LAV genomic RNA. It relates even more particularly to polypeptides comprising antigenic determinants included in the proteins encoded and expressed by the LAV genome occurring in nature. An additional object of the invention is to further provide means for the detection of proteins related to LAV virus, particularly for the diagnosis of AIDS or pre-AIDS or, to the contrary, for the detection of antibodies against the LAV virus or proteins related therewith, particularly in patients afflicted with AIDS or pre-AIDS or more generally in asymtomatic carriers and in blood-related products. Finally the invention also aims at providing immunogenic polypeptides, and more particularly protective polypeptides for use in the preparation of vaccine compositions against AIDS or related syndromes.

The present invention relates to additional DNA fragments, hybridizable with the genomic RNA of LAV as they will be disclosed hereafter, as well as with additional cDNA variants corresponding to the whole genomes of LAV viruses. It further relates to DNA recombinants containing said DNAs or cDNA fragments.

The invention relates more particularly to a cDNA variant corresponding to the whole of LAV retroviral genomes, which is characterized by a series of restriction sites in the order hereafter (from the 5' end to the 3' end).

The coordinates of the successive sites of the whole LAV genome (restriction map) are indicated hereafter too, with respect to the Hind III site (selected as of coordinate 1) which is located in the R region. The coordinates are estimated with an accuracy of ±200 bp:

| | |
|---|---|
| Hind III | 0 |
| Sac I | 50 |
| Hind III | 520 |
| Pst I | 800 |
| Hind III | 1100 |
| Bgl II | 1500 |
| Kpn I | 3500 |
| Kpn I | 3900 |
| Eco RI | 4100 |
| Eco RI | 5300 |
| Sal I | 5500 |
| Kpn 1 | 6100 |
| Bgl II | 6500 |
| Bgl II | 7600 |
| Hind III | 7850 |
| Bam HI | 8150 |
| Xho I | 8600 |
| Kpn I | 8700 |
| Bgl II | 8750 |
| Bgl II | 9150 |
| Sac I | 9200 |
| Hind III | 9250 |

Another DNA variant according to this invention optionally contains an additional Hind III approximately at the 5 550 coordinate.

Reference is further made to FIG. 1 which shows a more detailed restriction map of said whole-DNA (LJ19).

An even more detailed nucleotide sequence of a preferred DNA according to the invention is shown in FIGS. 6-12 hereafter.

The invention further relates to other preferred DNA fragments which will be referred to hereafter.

BRIEF DESCRIPTION OF THE DRAWINGS

Additional features of the invention will appear in the course of the non-limitative disclosure of additional features of preferred DNAs of the invention, as well as of preferred polypeptides according to the invention. Reference will further be had to the drawings in which:

Figure 5:
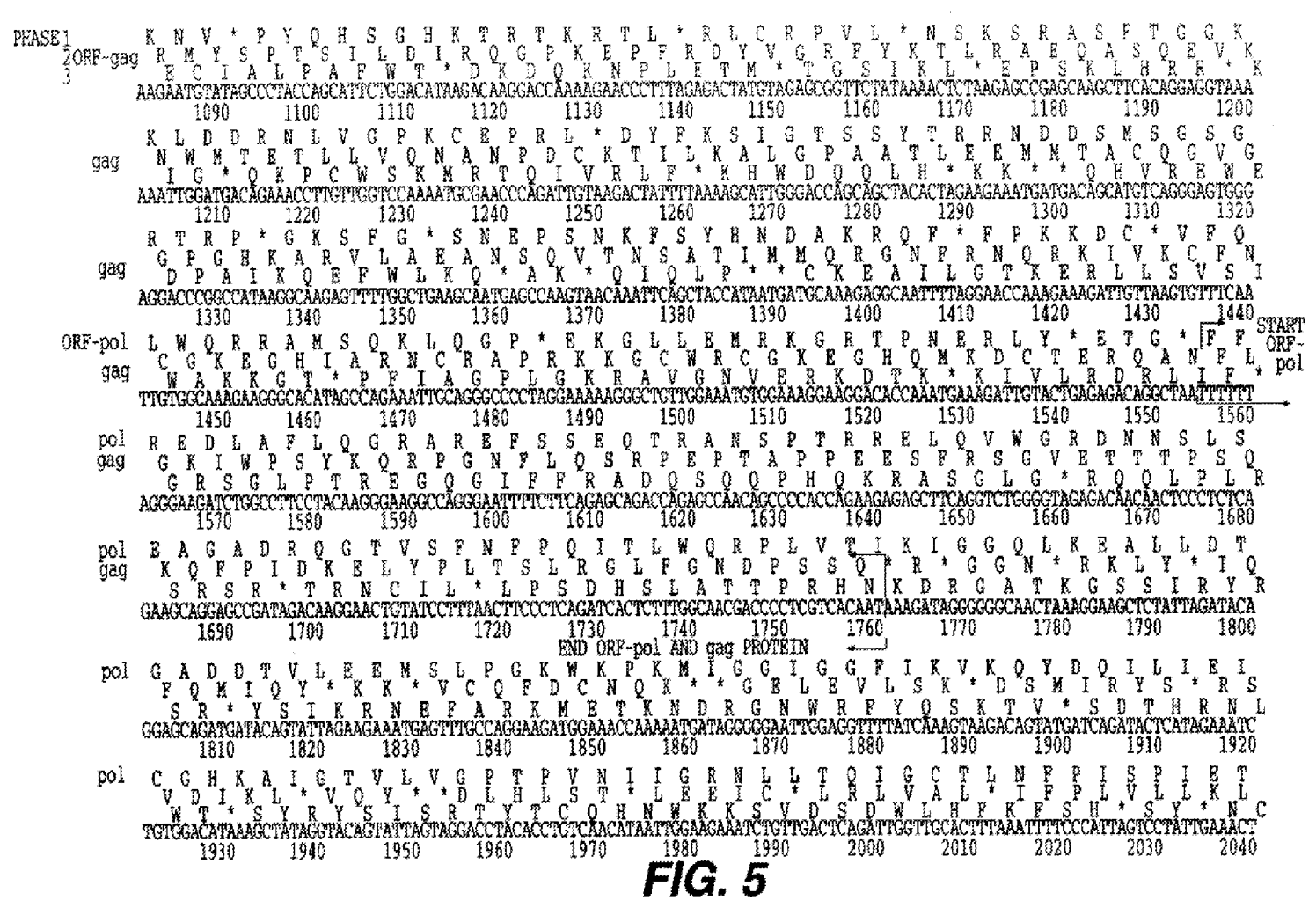
Figure 6:
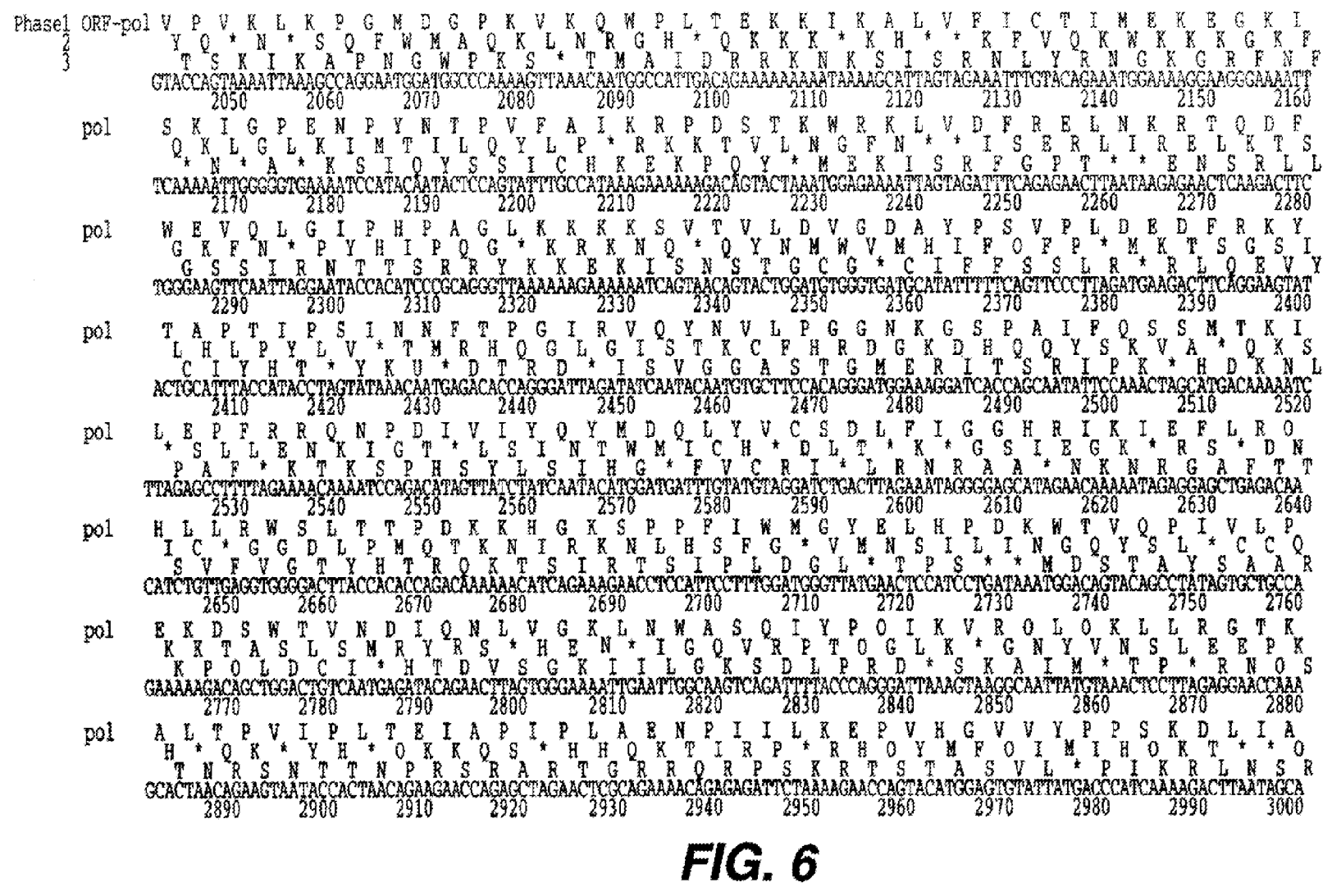
Figure 7:
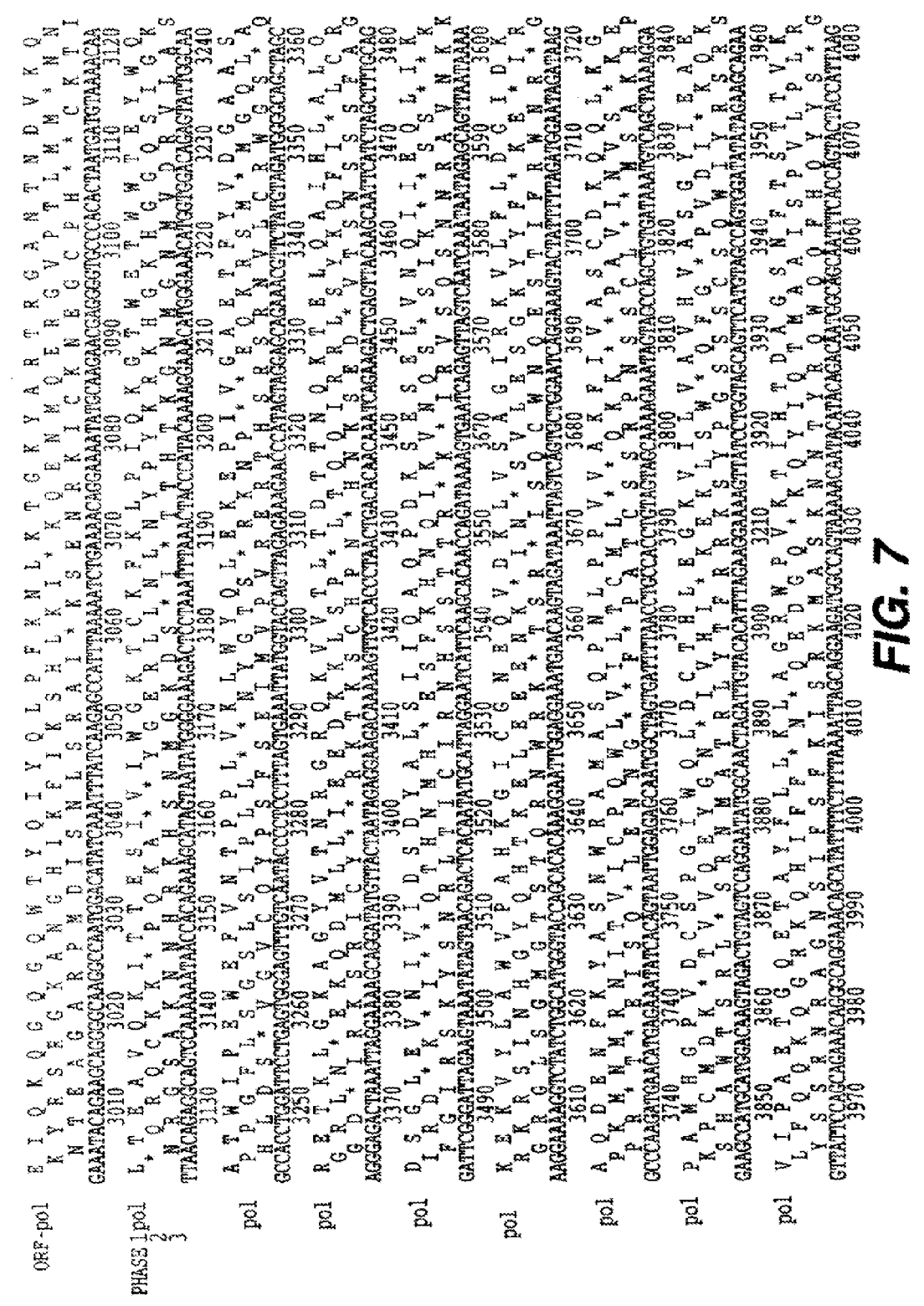
Figure 8:
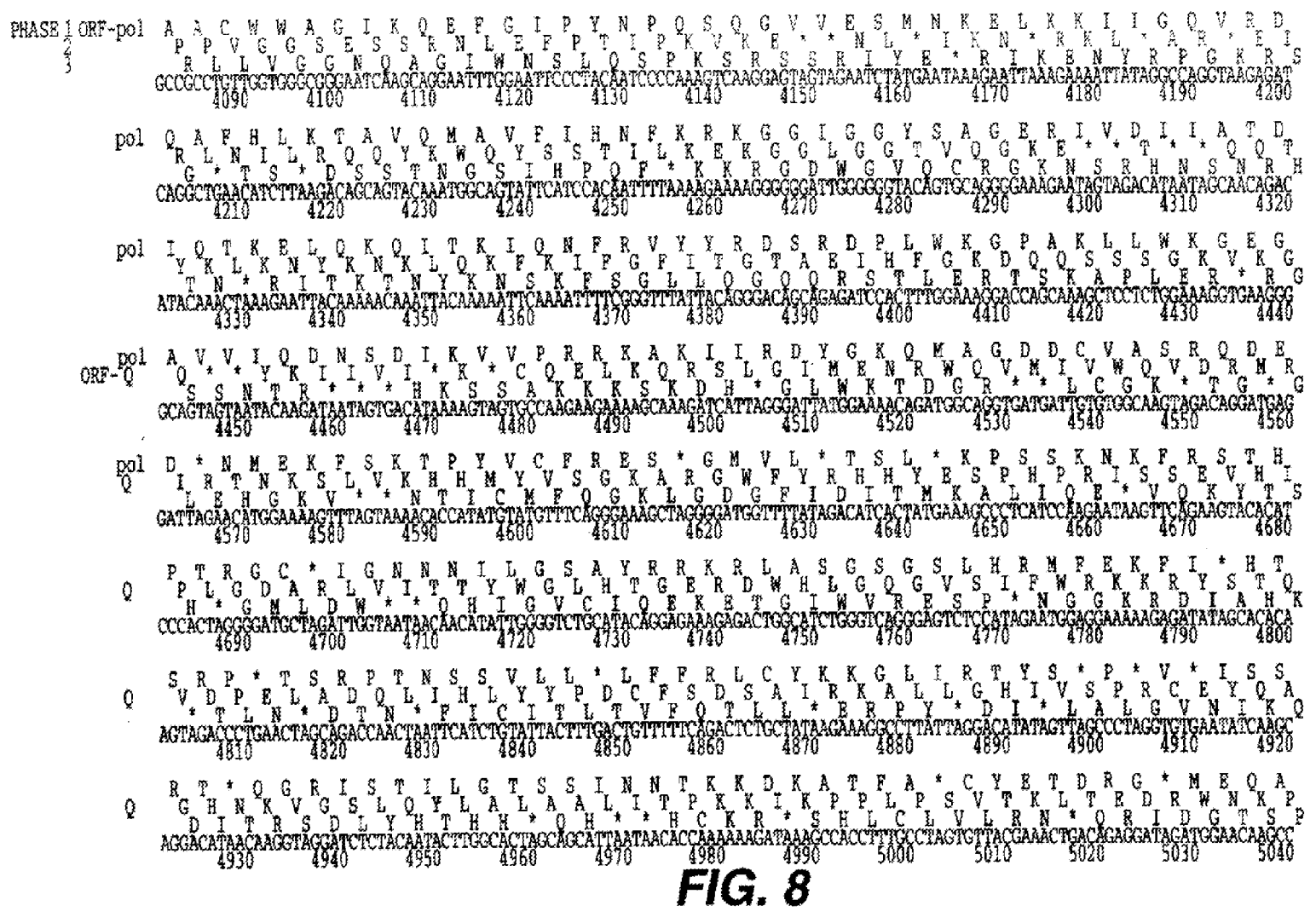
Figure 9:
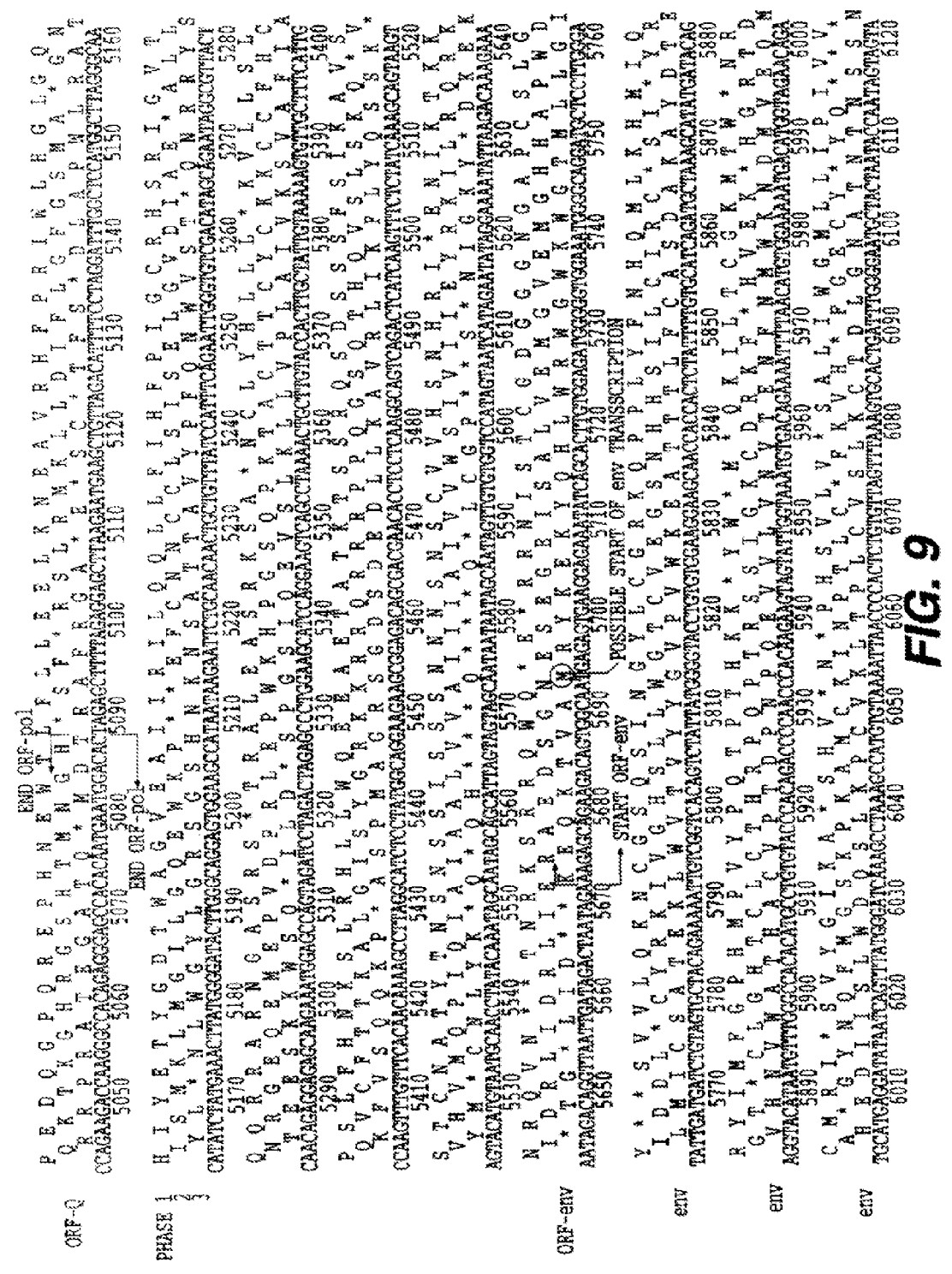
Figure 10:
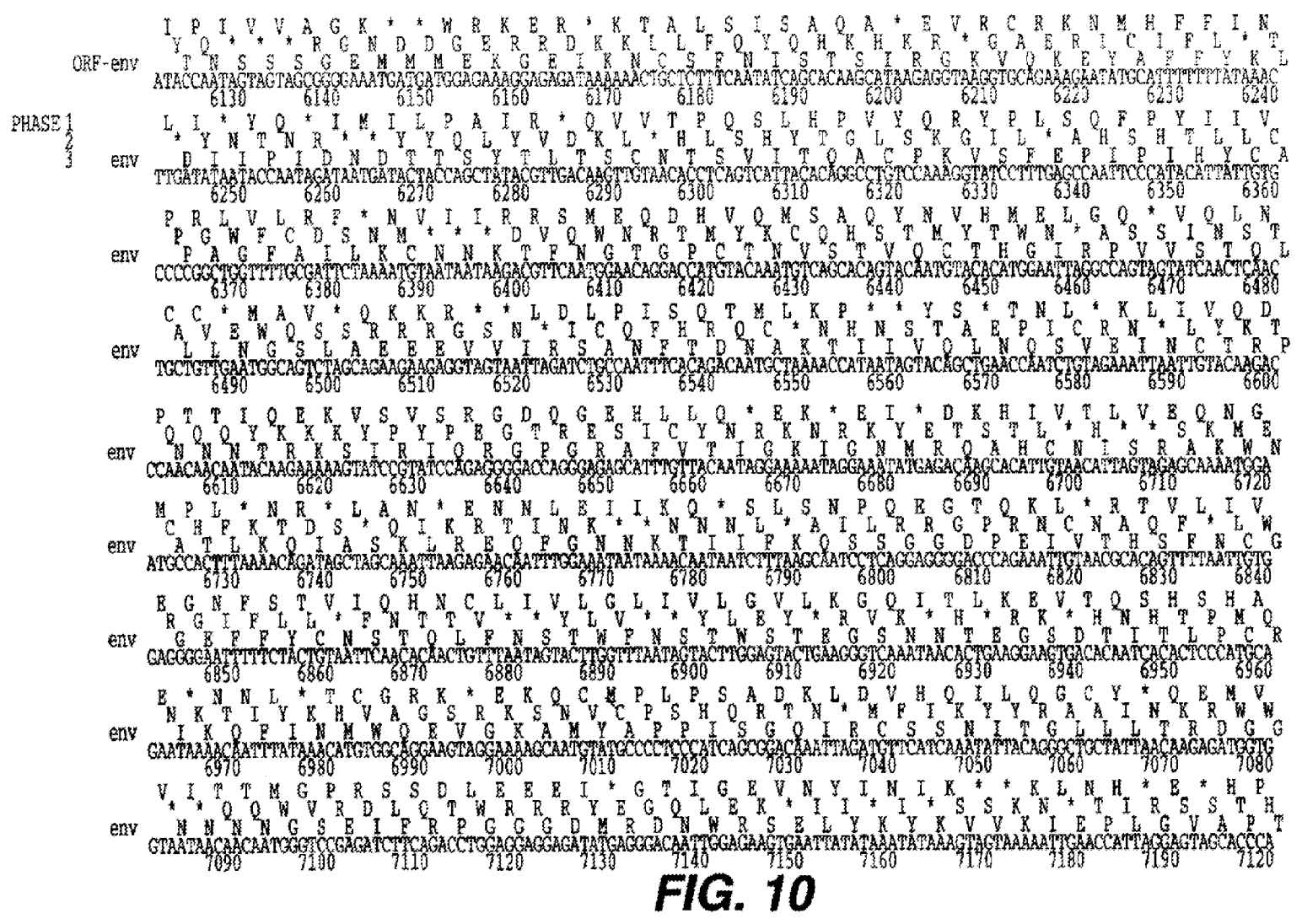
Figure 11:
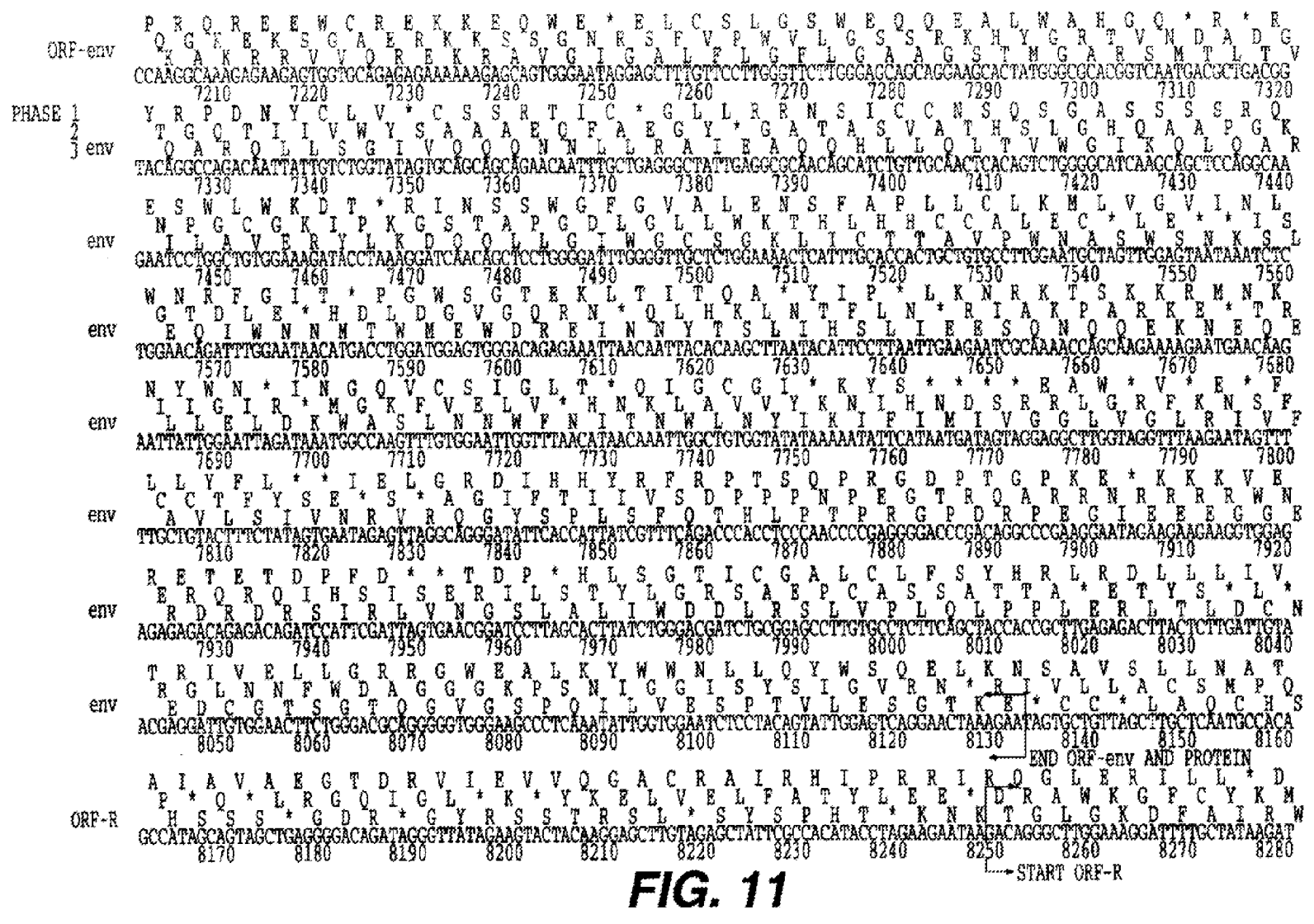
Figure 12:
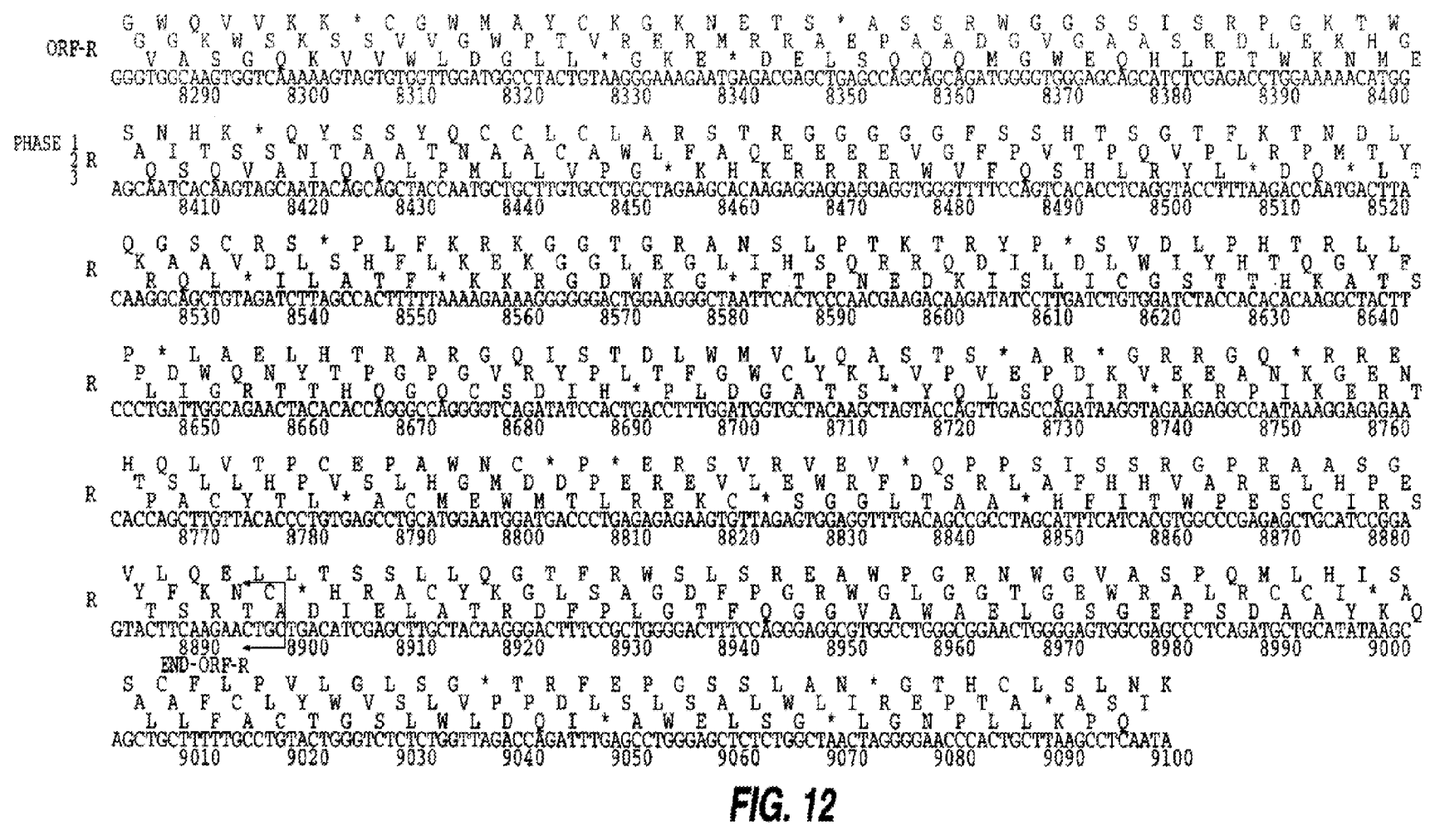

FIGS. 4-12 show the successive nucleotidic sequences of a complete LAV genome. The possible peptide sequences in relation to the three possible reading phases related to the nucleotide sequences shown are also indicated;

FIGS. 13-18 reiterate the sequence of part of the LAV genome containing the genes coding for the envelope proteins, with particular boxed peptidic sequences which corresponds to groups which normally carry glycosyl groups;

FIGS. 19-26 show the nucleotide sequence of a complete LAV genome;

DETAILED DESCRIPTION OF THE INVENTION

Figure 1:
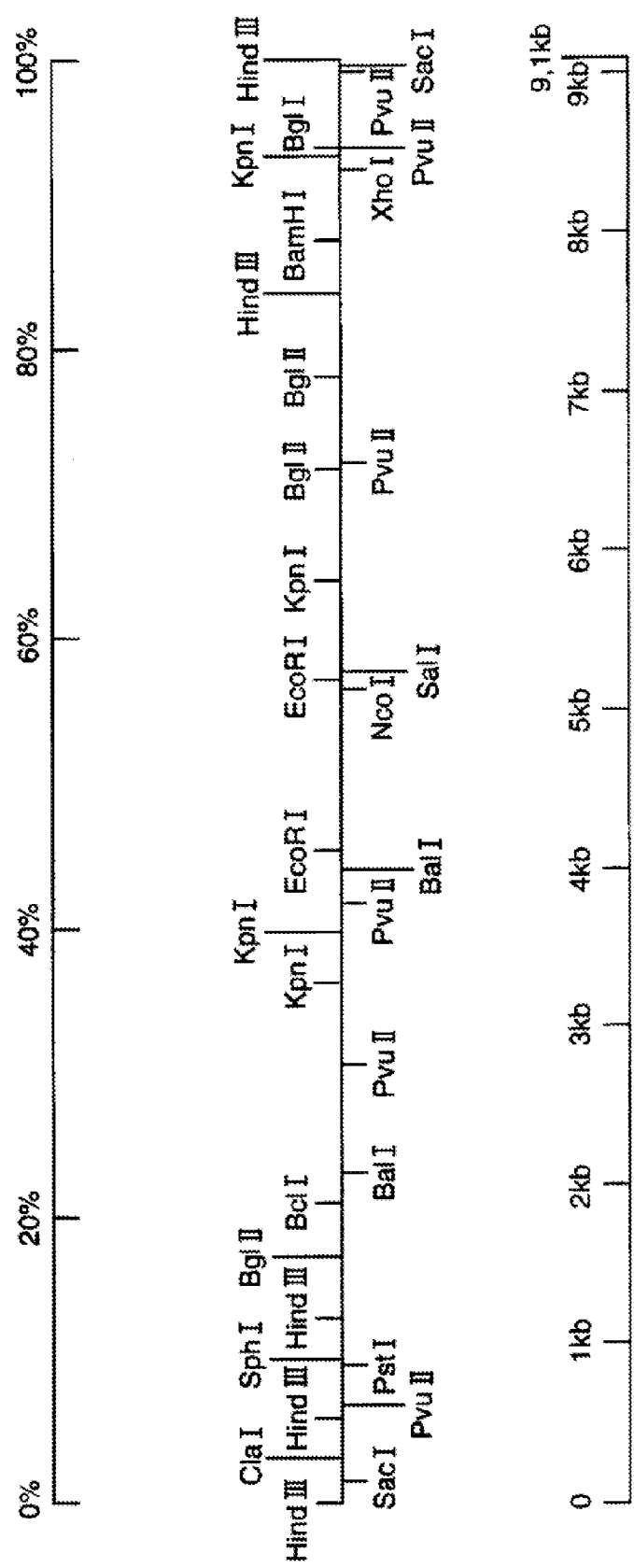
FIG. 1 is the restriction map of a complete LAV genome (clone A319)

The sequencing and determination of sites of particular interest was carried out on a phage recombinant corresponding to λJ19 disclosed in the above said British Patent application Nr. 84 23659. A method for preparing it is disclosed in that application.

The whole recombinant phage DNA of clone λJ19 (disclosed in the earlier application) was sonicated according to the protocol of DEININGER (1983), Analytical Biochem. 129, 216, the DNA was repaired by a Klenow reaction for 12 hours at 16° C. The DNA was electrophoresed through 0.8% agarose gel and DNA in the size range of 300-600 bp was cut out and electroeluted and precipitated. Resuspended DNA (in 10 mM Tris, pH 8:0.1 mM EDTA) was ligated into M13 mp8 RF DNA (cut by the restriction enzyme SmaI and subsequently alkaline phosphated), using T4 DNA- and RNA-ligases (Maniatis T et al (1982)-Molecular cloning—Cold Spring Harbor Laboratory). An *E. coli* strain designated as TG1 was used for further study. This strain has the following genotype Δlac pro, supE, thi.F'traD36, proAB, lacI$^q$, ZΔM15, r⁻.

This *E. coli* TGI strain has the peculiarity of enabling recombinants to be recognized easily. The blue colour of the cells transfected with plasmids which did not recombine with a fragment of LAV DNA is not modified. To the contrary, cells transfected by a recombinant plasmid containing a LAV DNA fragment yield white colonies. The technique which was used is disclosed in Gene (1983), 26, 101.

This strain was transformed with the ligation mix using the Hanahan method (Hanahan D (1983) J. Mol. Biol. 166, 557). Cells were plated out on tryptone-agarose plate with IPTG and X-gal in soft agarose. White plaques were either picked and screened or screened directly in situ using nitrocellulose filters. Their DNAs were hybridized with nick-translated DNA inserts of pUC18 Hind III subclones of λJ19. This permitted the isolation of the plasmids or subclones of λ which are identified in the table hereafter. In relation to this table it should also be noted that the designation of each plasmid is followed by the deposition number of a cell culture of *E. coli* TGI containing the corresponding plasmid at the "Collection Nationale des Cultures de Micro-organismes" (C.N.C.M.) of the Pasteur Institute in Paris, France. A non-transformed TGI cell line was also deposited at the C.N.C.M. under Nr. 1-364. All these deposits took place on Nov. 15, 1984. The sizes of the corresponding inserts derived from the LAV genome have also been indicated.

TABLE

Essential features of the recombinant plasmids

| pJ19 | 1 plasmid<br>Hind III - Sac I - Hind III | (I-365) | 0.5 kb |
|---|---|---|---|
| pJ19 | 17 plasmid<br>Hind III - Pst 1 - Hind III | (I-367) | 0.6 kb |
| pJ19 | 6 plasmid<br>Hind III (5')<br>Bam HI<br>Xho I<br>Kpn I<br>Bgl II<br>Sac I (3')<br>Hind III | (I-366) | 1.5 kb |
| pJ19 | 13 plasmid<br>Hind III (5')<br>Bgl II<br>Kpn I<br>Kpn I<br>Eco RI<br>Eco RI<br>Sal I<br>Kpn I<br>Bgl II<br>Bgl II<br>Hind III (3') | (I-368) | 6.7 kb |

Positively hybridizing M13 phage plates were grown up for 5 hours and the single-stranded DNAs were extracted.

M13 mp8 subclones of J19 DNAs were sequenced according to the dideoxy method and technology devised by Sanger et al. (Sanger et al (1977), Proc. Natl. Acad. Sci. USA, 74, 5463, and M13 cloning and sequencing handbook, AMERSHAM (1983), the 17-mer oligonucleotide primer α-$^{35}$SdATP (400 Ci/mmol, AMERSHAM), and 0.5×-5× buffer gradient gels (Biggen M. D. et al. (1983, Proc. Natl., Acad. Sci. USA, 50, 3963) were used. Gels were read and put into the computer under the programs of Staden (Staden R. (1982), Nucl. Acids Res. 10, 4731). All the appropriate references and methods can be found in the AMERSHAM M13 cloning and sequencing handbook.

The complete sequence of J19 was deduced from the experiments as further disclosed hereafter.

FIGS. 4-12 provide the DNA nucleotidie sequence of the complete genome of LAV. The numbering of the nucleotides starts from a left most Hind III restriction site (5' AAG.) of the restriction map. The numbering occurs in tens whereby the last zero number of each of the numbers occurring on the drawings is located just below the nucleotide corresponding to the nucleotides designated. I.e., the nucleotide at position 10 is T, the nucleotide at position 20 is C, etc.

Above each of the lines of the successive nucleotidic sequences there are provided three lines of single letters corresponding to the aminoacid sequence deduced from the DNA sequence (using the genetic code) for each at the three reading phases, whereby said single letters have the following meanings.

A: alanine
R: arginine
K: lysine
H: histidine
C: cysteine
M: mthionine
W: tryptophan
F: phenylalanine
V: tyrosine
L leucine
V: valine
I: isoleucine
G: glycine
I: threonine
S: serine
E: glutamic acid
D Aspartic acid
N: asparagine
Q: glutamine
P: proline The asterisk signs "*" correspond to stop codons (i.e. TAA, TAG and TGA).

Figure 4:
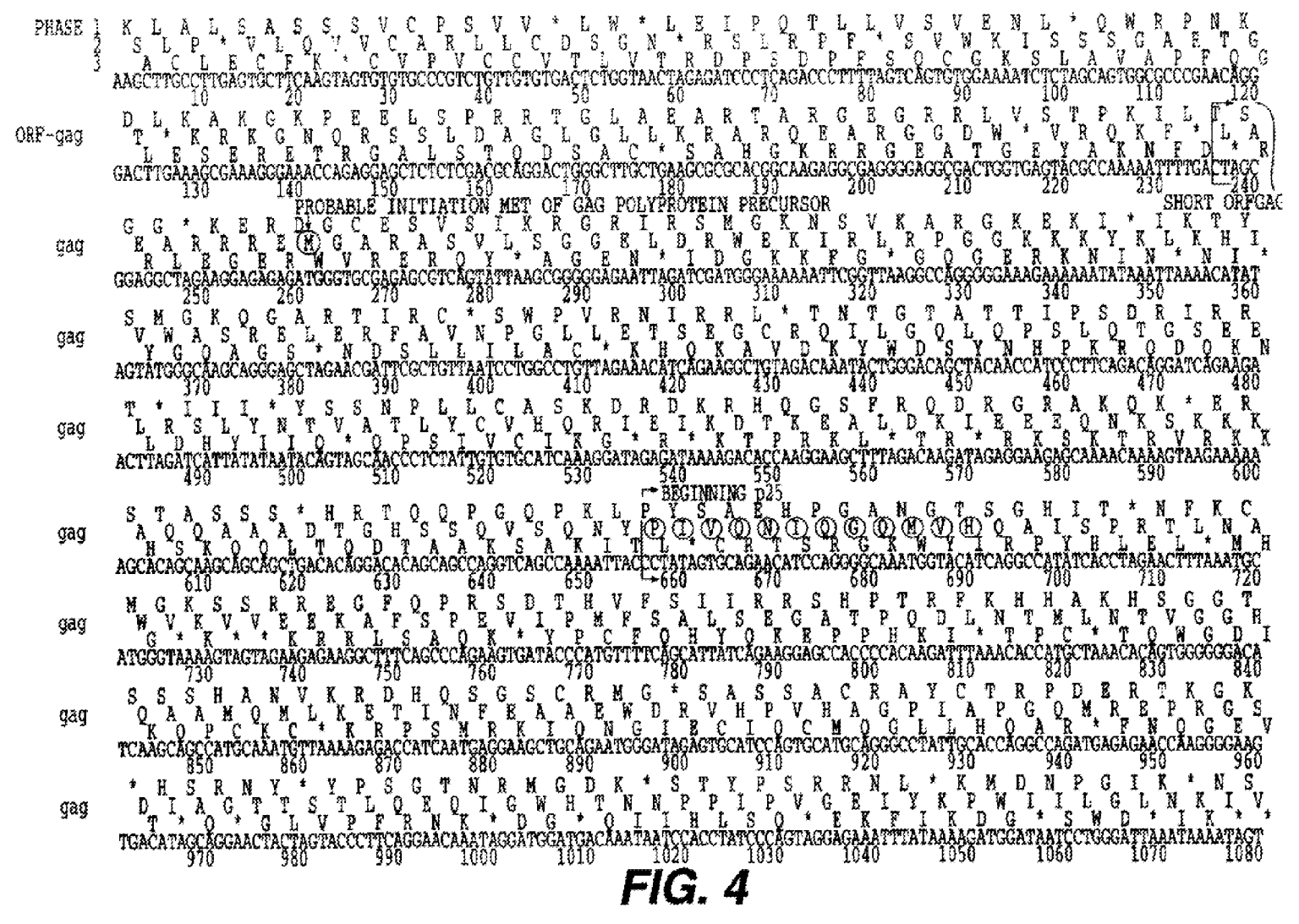

Starting above the first line of the DNA nucleotidic sequence of FIG. 4, the three reading phases are respectively marked "1", "2", "3" on the left handside of the drawing.

The same relative presentation of the three theoritical reading phases is then used all over the successives lines of the LAV nucleotidic sequence.

Figure 2:
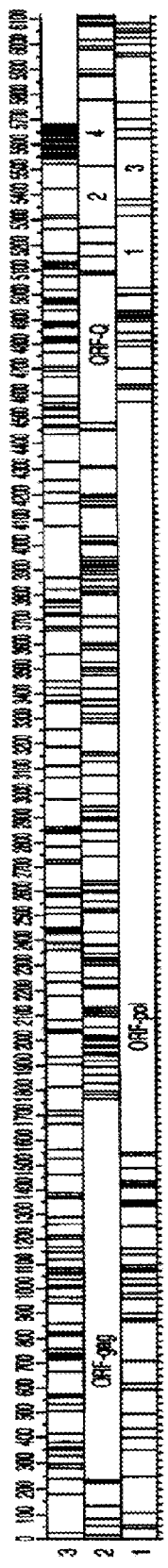
FIGS. 2 and 3 show diagrammatically parts of the three possible reading phases of LAV genomic RNA including the open reading frames (ORF) apparent in each of said reading phases.
Figure 3:
Figure 27:
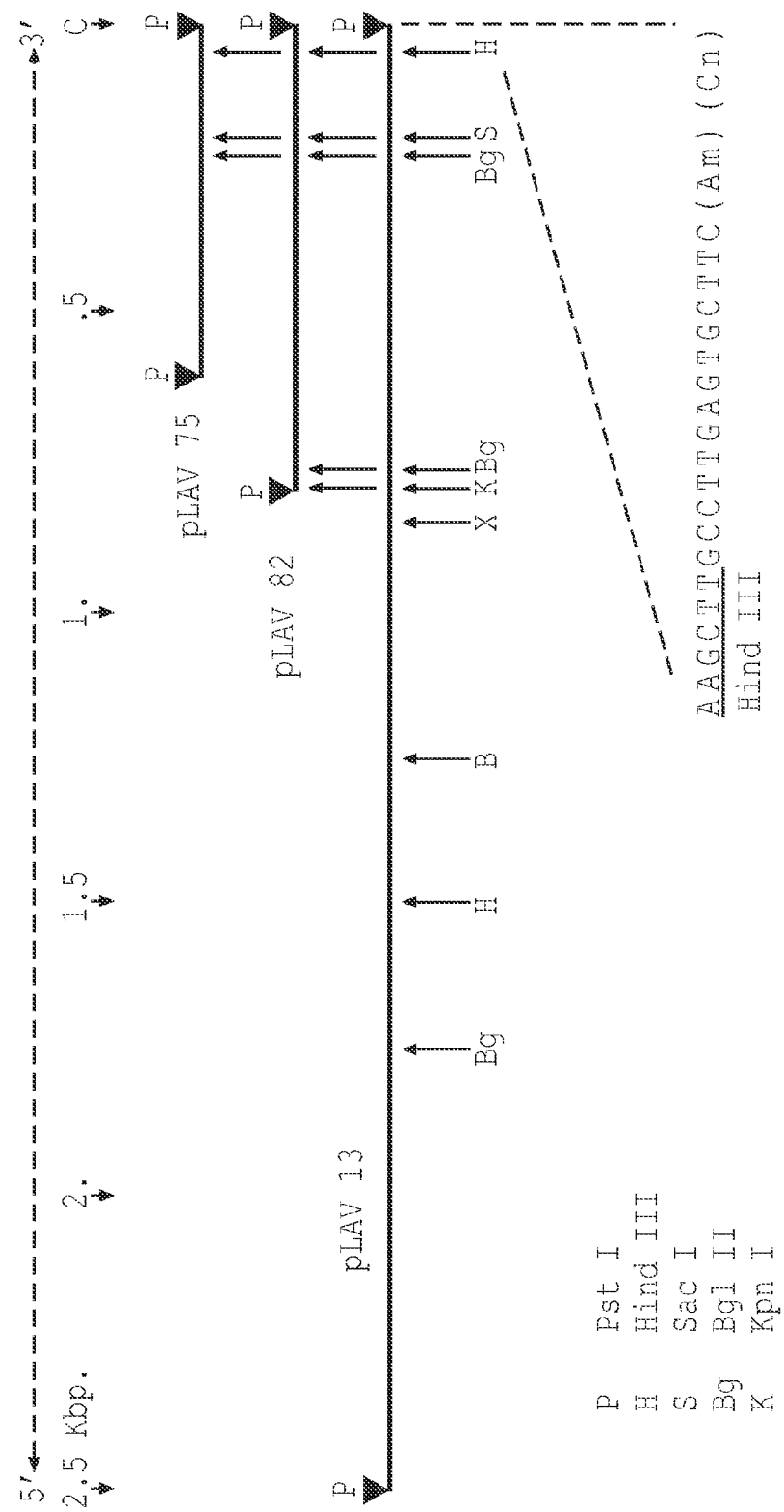
FIG. 27 shows restriction maps of preferred LAV inserts contained in plasmid recombinants.
Figure 28:
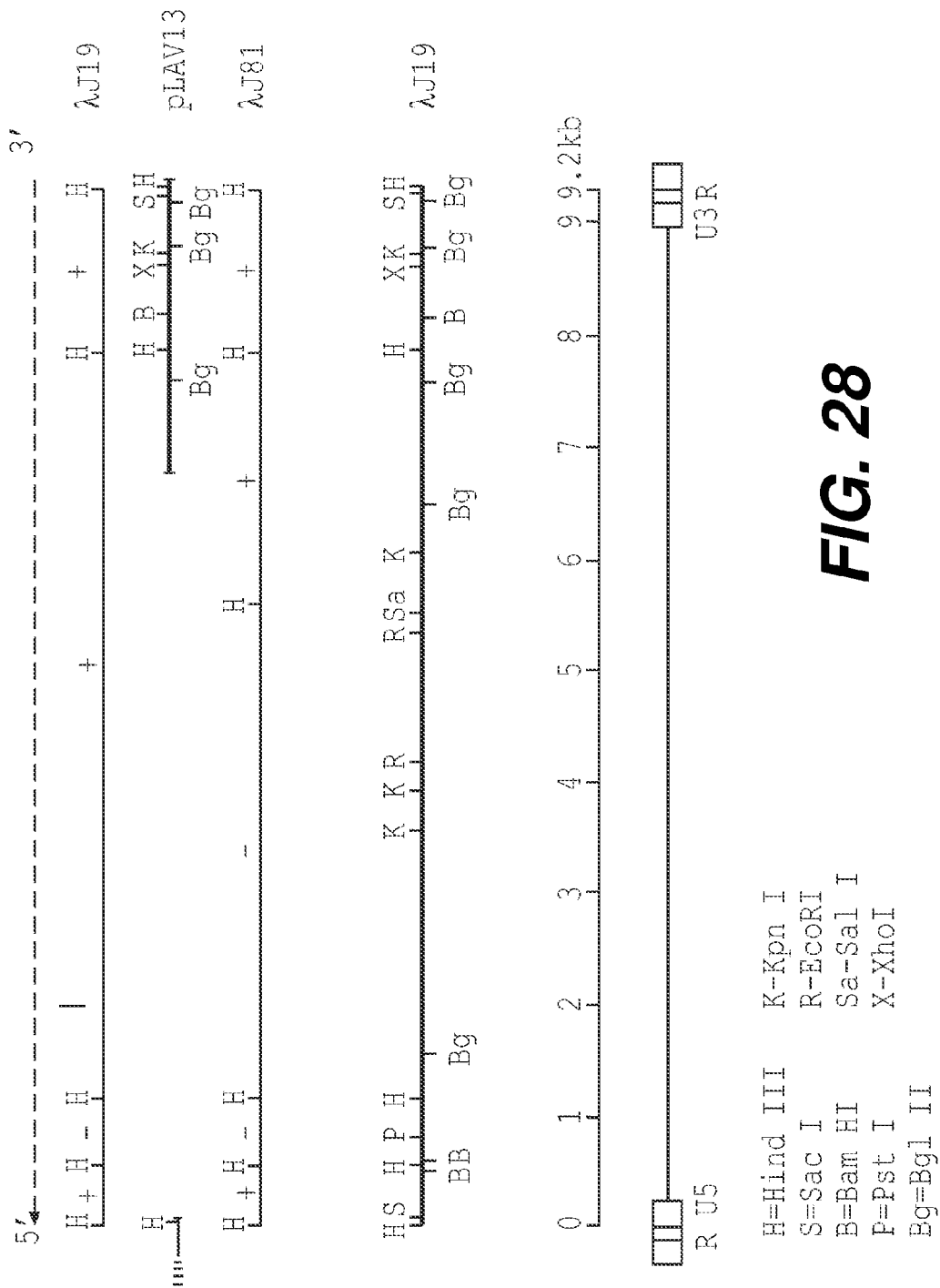
FIG. 28 shows restriction maps of complete LAV fragments.

FIGS. 2 and 3 provide a diagrammatized representation of the lengths of the successive open reading frames corresponding to the successive reading phases (also referred to by numbers "1", "2", and "3" appearing in the left handside part of FIG. 2). The relative positions of these open reading frames (ORF) with respect to the nucleotidic structure of the LAV genome is referred to by the scale of numbers representative of the respective positions of the corresponding nucleotides in the DNA sequence. The vertical bars correspond to the positions of the corresponding stop codons.

1) The "gag gene" (or ORF-gag)

The "gag gene" codes for core proteins. Particularly it appears that a genomic fragment (ORF-gag) thought to code for the core antigens including the p25, p18, and p13 proteins is located between nucleotidic position 236 (starting with 5' CTA GCG GAG 3') and nucleotidic position 1759 (ending by CTCG TCA CAA 3'). The structure of the peptides or proteins encoded by parts of said ORF is deemed to be that corresponding to phase 2.

The methionine aminoacid "M" coded by the ATG at position 260-262 is the probable initiation methionine of the gag protein precursor. The end of ORF-gag and accordingly of gag protein appears to be located at position 1759.

The beginning of p25 protein, thought to start by a P-I-V-Q-N-I-Q-G-Q-M-V-H . . . aminoacid sequence is thought to be coded for by the nucleotidic sequence CCTATA . . . , starting at position 656.

Hydrophilic peptides in the gag open reading frame are identified hereafter. They are defined starting from aminoacid 1=Met (M) coded by the ATG starting from 260-2 in the LAV DNA sequence.

Those hydrophilic peptides are

| | | |
|---|---|---|
| 12-32 | aminoacids | inclusive |
| 37-46 | " | " |
| 49-79 | " | " |
| 88-153 | " | " |
| 158-185 | " | " |
| 178-188 | " | " |
| 200-220 | " | " |
| 226-234 | " | " |
| 239-264 | " | " |
| 288-331 | " | " |
| 352-361 | " | " |
| 377-390 | " | " |
| 399-432 | " | " |
| 437-484 | " | " |
| 492-498 | " | " |

The invention also relates to any combination of these peptides.

2) The pol gene" (or ORF-pol)

FIGS. 4-12 also show that the DNA fragments extending from nucleotidic position 1555 (starting with 5'TTT TTT . . . 3' to nucleotidic position 5086 is thought to correspond to the pol gene. The polypeptidic structure of the corresponding polypeptides is deemed to be that corresponding to phase 1. It stops at position 4563 (end by 5'G GAT GAG GAT 3').

These genes are thought to code for the virus polymerase or reverse transcriptase.

The envelope gene (or ORF-env)

The DNA sequence thought to code for envelope proteins is thought to extend from nucleotidic position 5670 (starting with 5'AAA GAG GAG A . . . 0.3') up to nucleotidic position 8132 (ending by . . . A ACT AAA GAA 3'). Polypeptidic structures of sequences of the envelope protein correspond to those read according to the "phase 3" reading phase.

The start of env transcription is thought to be at the level of the ATG codon at positions 5691-5693.

Additional features of the envelope protein coded by the env genes appear on FIGS. 13-18. These are to be considered as paired FIGS. 13 and 14; 15 and 16; and 17 and 18, respectively.

It is to be mentioned that because of format difficulties.

FIG. 14 overlaps to some extent with FIG. 13.
FIG. 16 overlaps to some extent with FIG. 15.
FIG. 18 overlaps to some extent with FIG. 17.

Thus, for instance, FIGS. 13 and 14 must be considered together.

Particularly the sequence shown on the first line on the top of FIG. 13 overlaps with the sequence shown on the first line on the top of FIG. 14. In other words, the starting of the reading of the successive sequences of the any gene as represented in FIGS. 13-18 involves first reading the first line at the top of FIG. 13 then proceeding further with the first line of FIG. 14. One then returns to the beginning of the second line of FIG. 13, then again further proceed with the reading of the second line of page 14, etc. . . . . The same observations then apply to the reading of the paired FIGS. 15 and 16, and paired FIGS. 17 and 18, respectively.

The locations of neutralizing epitopes are further apparent in FIGS. 13-18, reference is more particularly made to the boxed groups of three letters included in the aminoacid sequences of the envelope proteins (reading phase 3) which can be designated generally by the formula N-X-S or N-X-T, wherein X is any other possible aminoacid. Thus, the initial protein product of the env gene is a glycoprotein of molecular weight in excess of 91,000. These groups are deemed to generally carry glycosylated groups. These N-X-S and N-X-T groups with attached glycosylated groups form together hydrophylic regions of the protein and are deemed to be located at the periphery of and to be exposed outwardly with respect to the normal conformation of the proteins. Consequently, they are considered as being epitopes which can efficiently be brought into play in vaccine compositions.

The invention thus concerns with more particularity peptide sequences included in the env-proteins and excisable therefrom (or having the same aminoacid structure), having sizes not exceeding 200 aminoacids.

Preferred peptides of this invention (referred to hereafter as a, b, c, d, e, f) are deemed to correspond to those encoded by the nucleotide sequences which extend respectively between the following positions:

| | | | | |
|---|---|---|---|---|
| a) | from about | 6095 | to about | 6200 |
| b) | " " | 6260 | " " | 6310 |
| c) | " " | 6390 | " " | 6440 |
| d) | " " | 6685 | " " | 6620 |
| e) | " " | 6860 | " " | 6930 |
| f) | " " | 7535 | " " | 7630 |

Other hydrophilic peptides in the any open reading frame are identified hereafter. they are defined starting from aminoacid 1=lysine (K) coded by the AAA at position 5670-2 in the LAV DNA sequence.

These hydrophilic peptides are

| | | |
|---|---|---|
| 8-23 | aminoacids | inclusive |
| 63-78 | " | " |
| 82-90 | " | " |
| 97-123 | " | " |
| 127-183 | " | " |
| 197-201 | " | " |
| 239-296 | " | " |
| 300-327 | " | " |
| 334-381 | " | " |
| 397-424 | " | " |
| 666-500 | " | " |
| 510-523 | " | " |
| 551-577 | " | " |
| 594-603 | " | " |
| 621-630 | " | " |
| 657-679 | " | " |

| | | | | | |
|---|---|---|---|---|---|
| 719-758 | " | | | " | |
| 780-803 | " | | | " | |

The invention also relates to any combination of these peptides.

4) The other ORFs

The invention further concerns DNA sequences which provide open reading frames defined as ORF-Q, ORF-R and as "1", "2", "3", "4", "5", the relative position of which appears more particularly in FIGS. 2 and 3.

These ORFs have the following locations:

| ORF-Q | phase | 1 | start | 4478 | stop | 5086 |
|---|---|---|---|---|---|---|
| ORF-R- | " | 2 | " | 8249 | " | 8896 |
| ORF-1 | " | 1 | " | 5029 | " | 5316 |
| ORF-2 | " | 2 | " | 5273 | " | 5515 |
| ORF-3 | " | 1 | " | 5383 | " | 5616 |
| ORF-4- | " | 2 | " | 5519 | " | 5773 |
| ORF-5" | " | 1 | " | 7966 | " | 8279 |

The LTR (long terminal repeats) can be defined as lying between position 8560 and position 160 (end extending over position 9097/1). As a matter of fact the end of the genome is at 9097 and, because of the LTR structure of the retrovirus, links up with the beginning of the sequence:

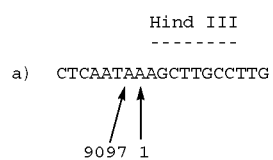

The invention concerns more particularly all the DNA fragments which have been more specifically referred to hereabove and which correspond to open reading frames. It will be understood that the man skilled in the art will be able to obtain them all, for instance, by cleaving an entire DNA corresponding to the complete genome of a LAV species, such as by cleavage by a partial or complete digestion thereof with a suitable restriction enzyme and by the subsequent recovery of the relevant fragments. The different DNAs disclosed in the earlier mentioned British Application can be resorted to also as a source of suitable fragments. The techniques disclosed hereabove for the isolation of the fragments which were then included in the plasmids referred to hereabove and which were then used for the DNA sequencing can be used.

Of course other methods can be used. Some of them have been exemplified in the earlier British Application, reference is for instance made to the following methods.

a) DNA can be transfected into mammalian cells with appropriate selection markers by a variety of techniques, calcium phosphate precipitation, polyethylene glycol, protoplast-fusion, etc.

b) DNA fragments corresponding to genes can be cloned into expression vectors for *E. coli* yeast- or mammalian cells and the resultant proteins purified.

c) The proviral DNA can be "shot-gunned" (fragmented), into procaryotic expression vectors to generate fusion polypeptides. Recombinant producing antigenically competent fusion proteins can be identified by simply screening the recombinants with antibodies against LAV antigens.

The invention also relates more specifically to cloned probes which can be made starting from any DNA fragment according to this invention, thus to recombinant DNAs containing such fragments, particularly any plasmids amplifiable in procaryotic or eucaryotic cells and carrying said fragments.

Using the cloned DNA fragments as a molecular hybridization probe—either by marking with radionucleotides or with fluorescent reagents—LAV virion RNA may be detected directly in the blood, body fluids and blood products (e.g. of the antihemophylic factors such as Factor VIII concentrates) and vaccines, i.e., hepatitis B vaccine. It has already been shown that whole virus can be detected in culture supernatants of LAV producing cells. A suitable method for achieving that detection comprises immobilizing virus onto said a support e.g. nitrocellulose filters, etc. disrupting the virion and hybridizing with labelled (radiolabelled or "cold" fluorescent- or enzyme-labelled) probes. Such an approach has already been developed for Hepatitis B virus in peripheral blood (according to SCOTTO J. et al. Hepatology (1983), 3, 379-384).

Probes according to the invention can also be used for rapid screening of genomic DNA derived from the tissue of patients with LAV related symptoms, to see if the proviral DNA or RNA is present in host tissue and other tissues.

A method which can be used for such screening comprise the following steps: extraction of DNA from tissue, restriction enzyme cleavage of said DNA, electrophoresis of the fragments and Southern blotting of genomic DNA from tissues, subsequent hybridization with labelled cloned LAV proviral DNA. Hybridization in situ can also be used.

Lymphatic fluids and tissues and other non-lymphatic tissues of humans, primates, and other mammalian species can also be screened to see if other evolutionarily related retrovirus exist. The methods referred to hereabove can be used, although hybridization and washings would be done under non stringent conditions.

The DNA according to the invention can be used also for achieving the expression of LAV viral antigens for diagnostic purposes.

The invention also relates to the polypeptides themselves which can be expressed by the different DNAs of the inventions, particularly by the ORFs or fragments thereof, in appropriate hosts, particularly procaryotic or eucaryotic hosts, after transformation thereof with a suitable vector previously modified by the corresponding DNAs.

These polypeptides can be used as diagnostic tools, particularly for the detection of antibodies in biological media, particularly in sera or tissues of persons afflicted with pre-AIDS or AIDS, or simply carrying antibodies in the absence of any apparent disorders. Conversely, the different peptides according to this invention can be used themselves for the production of antibodies, preferably monoclonal antibodies specific of the different peptides, respectively. For the production of hybridomas secreting said monoclonal antibodies conventional production and screening methods are used. These monoclonal antibodies, which themselves are part of the invention, then provide very useful tools for the identification and even determination of relative proportions of the different polypeptides or proteins in biological samples, particularly human samples containing LAV or related viruses.

Thus, all of the above peptides can be used in diagnostics as sources of immunogens or antigens free of viral particles, produced using non-permissive systems, and thus of little or no biohazard risk.

The invention further relates to the hosts (procaryotic or eucaryotic cells) which are transformed by the above mentioned recombinants and which are capable of expressing said DNA fragments.

Finally, it also relates to vaccine compositions whose active principle is to be constituted by any of the expressed antigens, i.e., whole antigens, fusion polypeptides, or oligopeptides in association with a suitable pharmaceutical or physiologically acceptable carrier.

Preferably, the active principles to be considered in that field consist of the peptides containing less than 250 amino acid units, preferably less than 150, as deducible for the complete genome of LAV, and even more preferably those peptides which contain one or more groups selected from N-X-S and N-X-T as defined above. Preferred peptides for use in the production of vaccinating principles are peptides (a) to (f) as defined above. By way of example having no limitative character, there may be mentioned that suitable dosages of the vaccine compositions are those which enable administration to the host, particularly human host ranging from 10 to 500 micrograms per kg, for instance 50 to 100 micrograms per kg.

For the purpose of clarity, FIGS. 19 to 26 are added reference may be made thereto in case of difficulties of reading blurred parts of FIGS. 4 to 12.

Needless to say, FIGS. 19-26 are merely a reiteration of the whole DNA sequence of the LAV genome.

Finally, the invention also concerns vectors for the transformation of eucaryotic cells of human origin, particularly lymphocytes, the polymerases of which are capable of recognizing the LTRs of LAV. Particularly said vectors are characterized by the presence of a LAV LTR therein, said LTR being then active as a promoter enabling the efficient transcription and translation in a suitable host of the above defined, of a DNA insert coding for a determined protein placed under its controls.

Needless to say, the invention extends to all variants of genomes and corresponding DNA fragments (ORFs) having substantially equivalent properties, all of said genomes belonging to retroviruses, which can be considered as equivalents of LAV.

The invention claimed is:

1. A kit for determining the absence of HIV-1 RNA in a biological sample comprising:
   a labeled HIV-1 nucleic acid;
   a first control sample comprising an HIV-1 RNA; and
   a second control sample that does not comprise HIV-1 RNA;
   wherein the kit determines the absence of HIV-1 RNA in the biological sample.

2. The kit of claim 1, wherein the nucleic acid is radioactively labeled.

3. The kit of claim 1, wherein the nucleic acid is enzymatically labeled.

4. The kit of claim 1, wherein the nucleic acid is fluorescently labeled.

* * * * *